(12) United States Patent
Ohkuchi et al.

(10) Patent No.: US 6,664,256 B1
(45) Date of Patent: Dec. 16, 2003

(54) PHENYLPYRIDAZINE COMPOUNDS AND MEDICINES CONTAINING THE SAME

(75) Inventors: Masao Ohkuchi, Tokorogawa (JP); Yoshinori Kyotani, Higashiyamato (JP); Hiromichi Shigyo, Fuchu (JP); Tomoyuki Koshi, Shiki (JP); Tadaaki Ohgiya, Tokorozawa (JP); Takayuki Matsuda, Higashimurayama (JP); Natsuyo Kumai, Fujimi (JP); Kyoko Kotaki, Sakado (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/612,953

(22) Filed: Jul. 10, 2000

(51) Int. Cl.$^7$ .................. A61K 31/50; A61K 31/501; C07D 237/14; C07D 237/24
(52) U.S. Cl. ............... 514/236.5; 514/247; 514/252.03; 544/238; 544/239; 544/114; 544/224
(58) Field of Search .................. 544/238, 239, 544/114, 224; 514/252.03, 247, 236.5

(56) References Cited

U.S. PATENT DOCUMENTS

| | | |
|---|---|---|
| 3,840,597 A | 10/1974 | Moore et al. |
| 4,954,518 A | 9/1990 | Takano et al. |

FOREIGN PATENT DOCUMENTS

| | | |
|---|---|---|
| EP | 0 376 288 | 7/1990 |
| EP | 0 628 550 | 12/1994 |
| WO | WO 93/14081 | 7/1993 |
| WO | WO 96/10012 | 4/1996 |
| WO | WO 97/05878 | 2/1997 |
| WO | WO 98/41511 | 9/1998 |
| WO | WO 99/10331 | 3/1999 |
| WO | WO 99/10332 | 3/1999 |
| WO | WO 99/25697 | 5/1999 |
| WO | WO 99/44995 | 9/1999 |
| WO | WO 00/24719 | 5/2000 |
| WO | WO 01/42241 | 6/2001 |

OTHER PUBLICATIONS

Livingston, *Journal of Cellular Biochemsitry*, 64, pp. 19–26, 1997.*
Taisho, 1 page, "KE–298," Jan. 19, 1999.
Takeshi Kamihara, The Japan Inflammation Academy, p. 75, "Antirheumatic Activites of KE–298, Having an Effect on IL–1," Jul. 20 and 21, 1990 (with English Translation).

V. Casini–Raggi, et al., Gastroenterology, vol. 109, pps. 812–818, "Anti–Inflammatory Effects of CGP 47969A, A Novel Inhibitor of Proinflammatory Cytokine Synthesis, in Rabbit Immune Colitis," 1995.
M. Tanaka, et al., Eur. J. Chem., vol. 31, pps. 187–198, "Hydroxyindole Derivatives as Inhibitors of IL–1 Generation. II. Synthesis and Pharmacological Activities of (E)–3–(7–Hydroxy–6–Methoxyindole–4–YL)–2–Methylpropenoic Acid Derivatives," 1996.
G. Ku, et al., Ctyokine, vol. 8, No. 5, pps. 377–386, "Interleukin–1β Converting Enzyme Inhibition Blocks Progression of Type II Collagen–Induced Arthritis in Mice," May 1996.
G. Nannini, et al., Eur. J. Med. Chem., vol. 14, No. 1, pps. 53–60, "Synthesis and Pharmacological Activtiy of Some 5, 6–Diphenyl–Pyridazines," Jan.–Feb. 1979.
J. Bondeson, et al., Biochemical Pharmacology, vol. 52, pps. 35–42,"Differntial Effects of Tenidap on the Zymosan– and Lipopolysaccharide–Induced Expression of mRNA For Proinflammatory Cytokines in Macrophages," 1996.

* cited by examiner

*Primary Examiner*—Emily Bernhardt
(74) *Attorney, Agent, or Firm*—Oblon, Spivak, McClelland, Maier & Neustadt, P.C.

(57) ABSTRACT

Phenylpyridazine compounds represented by the following formula (I):

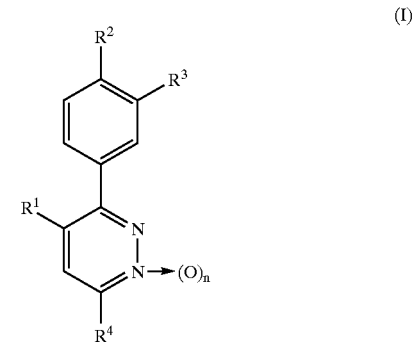

are provided, wherein $R^1$, $R^2$, $R^3$, $R^4$, and n are as defined herein having excellent inhibitory activity against interleukin-1β production, and useful in the treatment of prevention of diseases caused by stimulation of interleukin-1β production, such as immune system diseases, inflammatory diseases, and ischemic diseases.

18 Claims, No Drawings

PHENYLPYRIDAZINE COMPOUNDS AND MEDICINES CONTAINING THE SAME

TECHNICAL FIELD

The present invention relates to phenylpyridazine compounds having excellent inhibitory activity against interleukin-1β production and methods for the prevention and treatment of immune system diseases, inflammatory diseases, ischemic diseases and the like using the compounds, and medicines containing them as active ingredients.

BACKGROUND ART

In many diseases, such as rheumatism, arthritis, osteoporosis, inflammatory colitis, immune deficiency syndrome, ichoremia, hepatitis, nephritis, ischemic diseases, insulin-dependent diabetes mellitus, arterial sclerosis, Parkinson's disease, Alzheimer's disease, and leukemia, stimulation of the production of an inflammatory cytokine known as interleukin-1β is observed. Interleukin-1β serves to induce synthesis of an enzyme which is considered to take part in inflammation, such as collagenase and PLA2, and, when intra-articularly injected into animals, causes multiarticular destruction highly resembling rheumatoid arthritis. In the normal living body, on the other hand, interleukin-1β is controlled in activity by interleukin-1 receptors, soluble interleukin-1 receptor and interleukin-1 receptor antagonists.

From research conducted using recombinants of these bioactivity-inhibiting substances, anti-interleukin-1β antibodies, anti-receptor antibodies and knockout mice on various disease models, interleukin-1β has been found to play a pivotal role in the body, leading to an increasing potential of substances having interleukin-1β inhibitory activity as therapeutics for such diseases.

For example, immunosuppressors and steroids used for the treatment of rheumatism have been reported to inhibit the production of interleukin-1β. Even among medicines currently under development, KE298, a benzoylpropionic acid derivative [The Japanese Society of Inflammation (11th), 1990], for example, has been reported to have inhibitory activity against interleukin-1β production, although it is an immunoregulator. Inhibitory activity against interleukin-1β production is also observed in a group of compounds called "COX-2 selective inhibitors", including for example, nimesulide as a phenoxysulfonanilide derivative (DE 2333643), T-614 as a phenoxybenzopyran derivative (U.S. Pat. No. 4,954,518), and tenidap (oxyindole derivative) as a dual inhibitor (COX-1/5-LO).

For all of these compounds, however, interleukin-1β production inhibitory activity is not their primary action so that their inhibitory activity against interleukin-1β production is lower than their primary action.

In recent years, increasingly active research has been under way with a focus placed on inhibitory activity against interleukin-1β production. Production inhibitors can be classified into a group of compounds which inhibit the transmission process of an inflammatory signal to a cell nucleus and the transcription and translation process, and another group of compounds which inhibit an enzyme ICE that functions in the processing of a precursor of interleukin-1β. Known examples of compounds presumed to have the former action include SB203580 [Japanese Language Laid-Open (Kokai) Publication (PCT) No. HEI 7-503017], FR167653 (Eur. J. Pharm., 327, 169–175, 1997), E-5090 (EP 376288), CGP47969A (Gastroenterology, 109, 812–828, 1995), hydroxyindole derivatives (Eur. J. Med. Chem. 31, 187–198, 1996), and triarylpyrrole derivatives (WO 97/05878), while known examples of compounds presumed to have the latter action include VE-13,045 which is a peptide compound (Cytokine, 8(5), 377–386, 1996).

However, none of these compounds exhibit sufficient inhibitory activity against interleukin-1β production.

On the other hand, it is known that a variety of 5,6-diphenylpyridazine derivatives have analgesic and anti-inflammatory action (Eur. J. Med. Chem., 14, 53–60, 1979). However, absolutely nothing has been known with respect to inhibitory activity of these 5,6-diphenylpyridazine derivatives against interleukin-1β production.

As pyridazine derivatives having inhibitory activity against interleukin-1β production, some pyridazine derivatives have been published recently in JP 7-69894, WO 9841511, WO 9910331, WO 9910332, WO 9925697 and WO 9944995. They are, however, different in chemical structure from the compounds according to the present invention.

There is thus a need for compounds capable of inhibiting interleukin-1β production.

SUMMARY OF THE PRESENT INVENTION

Accordingly, one object of the present invention is to provide a compound having excellent inhibitory activity against interleukin-1β production.

A further object of the present invention is to provide a method for the treatment of diseases and conditions caused by stimulation of interleukin-1β production.

A further object of the present invention is to provide a pharmaceutical composition useful in treatment of diseases and conditions caused by stimulation of interleukin-1β production.

These and other objects of the present invention have been satisfied by the discovery of phenylpyridazine compounds of formula (I):

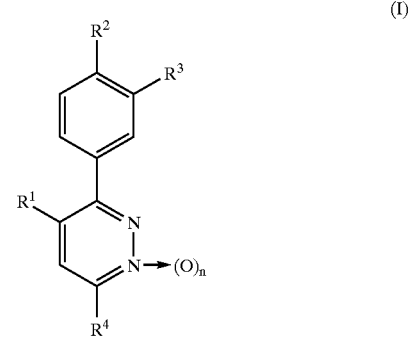

wherein
R1, R2, R3, R4 and n have the meanings disclosed herein, which has excellent inhibitory activity against interleukin-1β production, and their use in pharmaceutical compositions and methods for treating diseases caused by stimulation of interleukin-1β production.

DETAILED DESCRIPTION OF THE PREFERRED EMBODIMENTS

The present invention relates to pyridazine compounds represented by formula (I) having excellent inhibitory activity against interleukin-1β production and useful as medicines for the prevention and treatment of immune system diseases, inflammatory diseases and ischemic diseases.

The phenylpyridazine compound of the present invention is represented by the following formula (I):

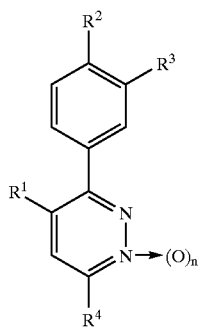

wherein
- $R^1$ represents a substituted or unsubstituted phenyl group or a substituted or unsubstituted pyridyl group,
- $R^2$ represents a lower alkoxy group, a lower alkylthio group, a lower alkylsulfinyl group or a lower alkylsulfonyl group;
- $R^3$ represents a hydrogen atom or a lower alkoxy group, or $R^2$ and $R^3$ may be fused together to form an alkylenedioxy group,
- $R^4$ represents hydrogen, halogen, cyano, carboxy, substituted or unsubstituted lower alkyl, substituted or unsubstituted lower alkenyl, substituted or unsubstituted lower alkylthio, substituted or unsubstituted lower alkylsulfinyl, substituted or unsubstituted lower alkylsulfonyl, substituted or unsubstituted lower alkylsulfonyloxy, substituted or unsubstituted aryl, substituted or unsubstituted phenoxy, substituted or unsubstituted phenylthio, substituted or unsubstituted phenylsulfinyl, substituted or unsubstituted phenylsulfonyl, substituted or unsubstituted pyridyloxy, substituted or unsubstituted morpholino, substituted or unsubstituted morpholinocarbonyl, substituted or unsubstituted piperidinocarbonyl, substituted or unsubstituted 1-piperazinylcarbonyl or substituted or unsubstituted amino, and
- n is 0 or 1,
- with the proviso that when $R^1$ is 4-methoxyphenyl group, $R^2$ is a methoxy group and $R^3$ is a hydrogen atom, $R^4$ can not be hydrogen or halogen, and also $R^1$ can not be 4-(methylsulfonyl)phenyl or 4-(aminosulfonyl)phenyl;

or a salt thereof.

The present invention also provides a composition comprising the phenylpyridazine compound (I) or the salt thereof as an effective ingredient, in a suitable pharmaceutically acceptable carrier.

Moreover, the present invention also provides a method for treating a disease caused by stimulation of interleukin-1β production, which comprises administering to a subject in need thereof, an effective amount of the phenylpyridazine compound (I) or the salt thereof, either alone or as a composition in a pharmacologically acceptable carrier.

Within the context of the present invention, the term "lower alkyl" represents alkyl groups having from 1 to 6 carbons and being either linear, branched or cyclic.

Illustrative of the lower alkyl group and the lower alkyl moieties in the lower alkoxy group, lower alkylthio group, lower alkylsulfinyl group, lower alkylsulfonyl group and lower alkylsulfonyloxy group as used herein are linear, branched or cyclic lower alkyl groups having 1 to 6 carbon atoms, such as, methyl, ethyl, n-propyl, isopropyl, n-butyl, isobutyl, t-butyl, n-pentyl, 2-methyl butyl, 2,2-dimethyl propyl, cyclopentyl, cyclohexyl, n-hexyl, 2-methyl pentyl, 3-methyl pentyl, 2,2-dimethyl butyl and 2,3-dimethylbutyl groups. Examples of the halogen atom can include fluorine, chlorine, bromine and iodine atoms.

Examples of one or more substituent groups on the substituted phenyl or pyridyl group represented by $R^1$ in the formula (I) include halogen, hydroxyl, alkyl, lower alkoxy and phenylthio groups, with halogen, lower alkoxy or phenylthio groups being particularly preferred. As the halogens, fluorine or chlorine are preferred, and as lower alkoxy groups, methoxy is preferred. These substituent groups are preferably substituted to the 4-position of a phenyl group, although they may be present at any other position as desired. A preferred $R^1$ group is a pyridyl group or a phenyl group substituted by one or more halogens, lower alkoxy or phenylthio groups. More preferred $R^1$ groups are 4-methoxyphenyl, 4-pyridyl, phenyl, 4-fluorophenyl, 4-chlorophenyl or 4-(phenylthio)phenyl.

As the lower alkyl moiety in lower alkoxy, lower alkylthio, lower alkylsulfinyl or lower alkylsulfonyl groups represented by $R^2$, methyl is especially preferred. Most preferred $R^2$ groups are methoxy, methylthio or methylsulfonyl.

As the lower alkoxy group represented by $R^3$, methoxy is particularly preferred.

Further, when $R^2$ and $R^3$ combine to form an alkylenedioxy group, ethylenedioxy is preferred.

Examples of one or more substituent groups on the substituted lower alkyl groups represented by $R^4$ include halogen, hydroxy, cyano, nitro, amino, carboxy, and substituted or unsubstituted aminocarbonyl groups. Illustrative of one or more substituent groups on the aminocarbonyl group are hydroxyl and lower alkyl groups. Examples of one or more substituent groups on the substituted lower alkenyl group represented by $R^4$ include halogen and aryl groups. Examples of the lower alkenyl group include linear, branched or cyclic lower alkenyl groups having 1 to 6 carbon atoms, with an allyl group being particularly preferred. Examples of one or more substituent groups on substituted lower alkylthio, substituted lower alkylsulfinyl, substituted lower alkylsulfonyl or substituted lower alkylsulfonyloxy represented by $R^4$ include aryl groups. Illustrative of one or more substituent groups on the substituted aryl group represented by $R^4$ are halogen, lower alkyl, lower alkoxy, cyano, nitro, and amino groups, with halogen and lower alkyl groups being particularly preferred. Examples of the aryl group include phenyl and pyridyl, with phenyl being particularly preferred. Examples of one or more substituent groups on the substituted phenoxy group represented by $R^4$ include halogen, cyano, nitro, amino, lower alkyl and lower alkoxy groups, among which halogen, cyano, nitro and lower alkoxy groups are particularly preferred. Illustrative of one or more substituent groups on substituted phenylthio, substituted phenylsulfinyl or substituted phenylsulfonyl groups represented by $R^4$ are halogen, lower alkyl, lower alkoxy, cyano, nitro and amino groups, with halogen being particularly preferred. Illustrative of one or more substituent groups on the substituted pyridyloxy group represented by $R^4$ are halogen, lower alkyl, lower alkoxy, cyano, nitro, and amino groups. Illustrative of one or more substituent groups on substituted morpholino, substituted morpholinocarbonyl or substituted piperidinocarbonyl groups represented by $R^4$ are halogen, lower alkyl, lower alkoxy, cyano and nitro groups. Illustrative of one or more substituent groups on the substituted 1-piperazinylcarbonyl group represented by $R^4$ are halogen, lower alkyl, lower alkoxy, cyano, nitro and amino groups, with lower alkyl groups being particularly preferred. Illustrative of one or more substituent groups on the substituted amino group represented by $R^4$ are lower alkyl, substituted or unsubstituted phenyl, benzyl, or acyl groups, among which lower alkyl, substituted or unsubstituted phenyl and benzyl groups are preferred. Examples of the substituent groups on the phenyl group include halogen, cyano, nitro, amino and lower alkoxy groups, with halogen and alkoxy groups being preferred.

Preferred group as $R^4$ is hydrogen; halogen; cyano; carboxyl; lower alkyl, which may be substituted by one or more groups selected from hydroxyl, carboxyl or substituted or unsubstituted aminocarbonyl groups; lower alkenyl; lower alkylthio; lower alkylsulfonyl; lower alkylsulfonyloxy; phenyl; phenoxy, which may be substituted by one or more groups selected from halogens, cyano, nitro or lower alkoxy groups; phenylthio, which may be substituted by one or more halogen atoms; pyridyloxy; morpholino; morpholinocarbonyl; 1-piperazinylcarbonyl, which may be substituted by one or more lower alkyl groups; or amino, which may be substituted by one or more members selected from lower alkyl, substituted or unsubstituted phenyl, or benzyl groups.

In the phenylpyridazine derivative of formula (I) according to the present invention, $R^1$ represents a substituted or unsubstituted phenyl group or a pyridyl group, $R^2$ represents lower alkoxy, lower alkylthio or lower alkylsulfonyl, $R^3$ represents hydrogen or lower alkoxy, or $R^2$ and $R^3$ may be fused together to form an alkylenedioxy group. $R^4$ represents hydrogen, halogen, cyano, carboxy, substituted or unsubstituted lower alkyl, lower alkenyl, lower alkylthio, lower alkylsulfonyl, a lower alkyl sulfonyloxy, substituted or unsubstituted aryl, substituted or unsubstituted phenoxy, a substituted or unsubstituted phenylthio, pyridyloxy, morpholino, morpholinocarbonyl, substituted or unsubstituted 1-piperazinylcarbonyl or substituted or unsubstituted amino, and n represens 0 or 1, with a proviso that a phenylpyridazine derivative of the formula (I) in which $R^4$ is a hydrogen or halogen atom, $R^1$ is 4-methoxyphenyl, $R^2$ is methoxy and $R^3$ is hydrogen is excluded; or that a phenylpyridazine derivative of the formula (I) in which $R^1$ is 4-(methylsulfonyl)phenyl or 4-(aminosulfonyl)phenyl is excluded. More preferred specific examples of the phenylpyridazine compound (I) according to the present invention include 3,4-bis(4-methoxyphenyl)-6-(phenoxy)pyridazine, 3,4-bis(4-methoxyphenyl)-6-(2,3-difluorophenoxy)pyridazine, 3,4-bis(4-methoxyphenyl)-6-(2,5-difluorophenoxy)pyridazine, 3,4-bis(4-methoxyphenyl)-6-(2,6-difluorophenoxy)pyridazine, 3,4-bis(4-methoxyphenyl)-6-(3,4-difluorophenoxy)pyridazine, 3,4-bis(4-methoxyphenyl)-6-(2,3,5,6-tetrafluorophenoxy)pyridazine, 3,4-bis(4-methoxyphenyl)-6-(2,3,4,5,6-pentafluorophenoxy)pyridazine, 3,4-bis(4-methoxyphenyl)-6-(3,4,5-trichlorophenylthio)pyridazine, 3,4-bis(4-methoxyphenyl)-6-(4-methoxyphenoxy)pyridazine, 3,4-bis(4-methoxyphenyl)-6-(4-nitrophenoxy)pyridazine, 3,4-bis(4-methoxyphenyl)-6-(2-cyanophenoxy)pyridazine, 3,4-bis(4-methoxyphenyl)-6-(3-cyanophenoxy)pyridazine, 6-(2,4-difluorophenoxy)-3-(4-methoxyphenyl)-4-(4-pyridyl)pyridazine, 6-(2,3-difluorophenoxy)-3-(4-methoxyphenyl)-4-phenylpyridazine, 6-(2,4-difluorophenoxy)-3-(4-methoxyphenyl)-4-phenylpyridazine, 3-(4-methoxyphenyl)-6-(2,3,4,5,6-pentafluorophenoxy)-4-phenylpyridazine, 3-(4-methylthiophenyl)-6-phenylthio-4-(4-phenylthiophenyl)pyridazine, 4-(4-chlorophenyl)-6-(2,4-difluorophenoxy)-3-[4-(methylthio)phenyl]pyridazine, 3,4-bis(4-methoxyphenyl)-6-cyanopyridazine, and 6-cyano-3-(4-methoxyphenyl)-4-phenylpyridazine.

No particular limitation is imposed on the process for the preparation of the phenylpyridazine compound (I) or a salt thereof of the present invention, and various processes, which have conventionally been used for the synthesis of pyridazine derivatives, and their modifications can be used. For example, the phenylpyridazine compound (I) or a salt thereof of the present invention can be prepared in accordance with the reaction schemes of any one of the following preparation processes 1–5.

(Preparation Process 1)

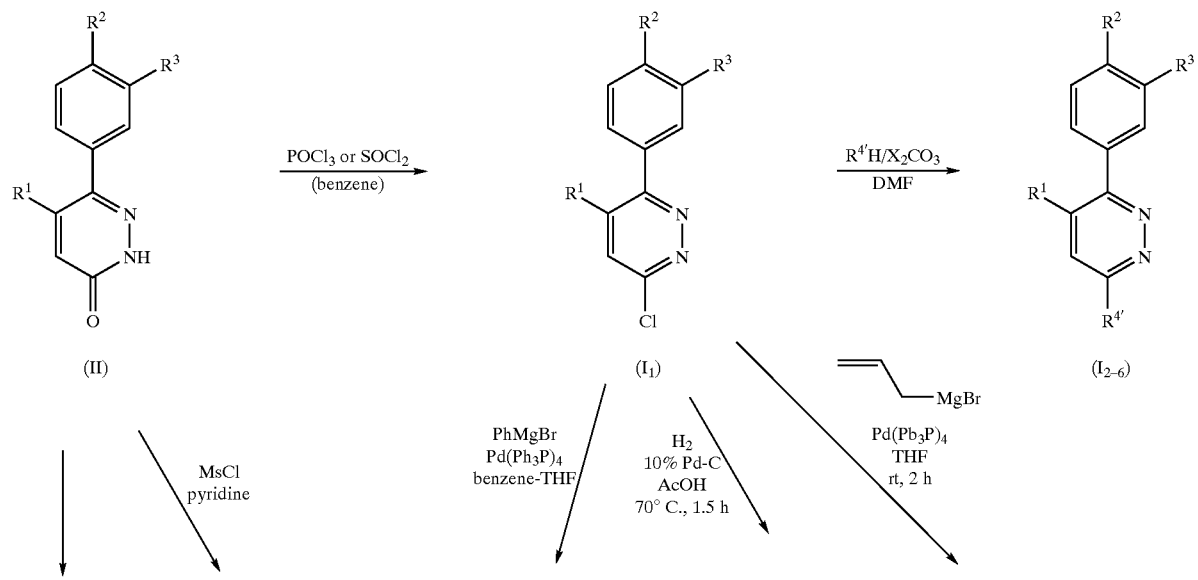

-continued

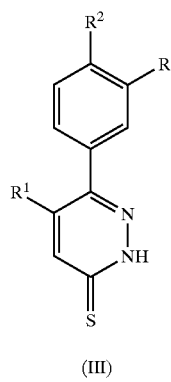 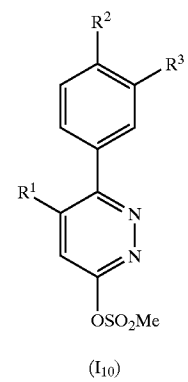 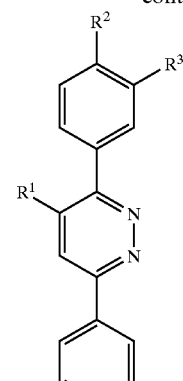 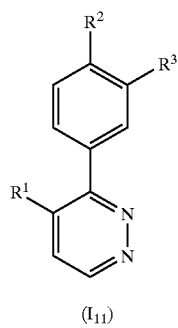 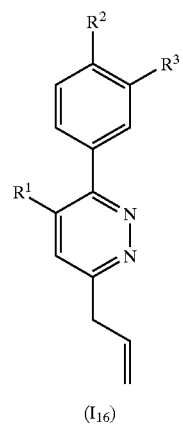

(III) (I₁₀) (I₇) (I₁₁) (I₁₆)

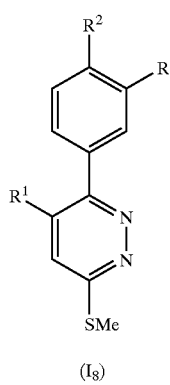 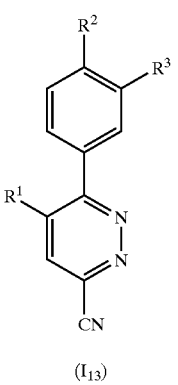 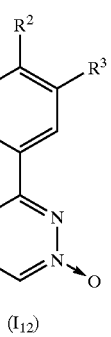 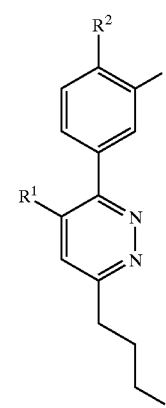 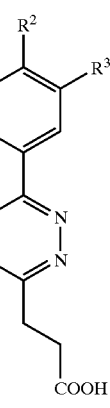

(I₈) (I₁₃) (I₁₂) (I₁₇) (I₁₈)

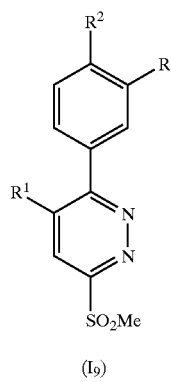 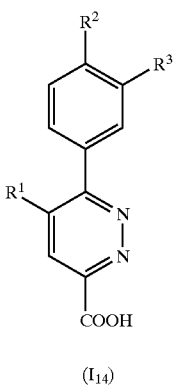 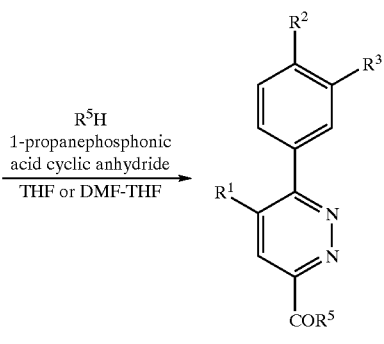 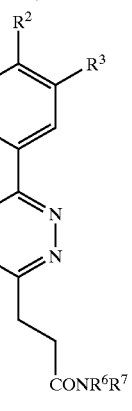

(I₉) (I₁₄) (I₁₅) (I₁₉)

wherein $R^1$, $R^2$ and $R^3$ have the same meanings as defined above, $R^5$ represents substituted or unsubstituted morpholino, substituted or unsubstituted piperidino, substituted or unsubstituted 1-piperazinyl, or the like, and $R^6$ and $R^7$ each independently represent hydrogen, hydroxy, lower alkyl, or the like.

In preparation process 1, starting material compounds (II) and (III) can be prepared by known processes (WO 9925697).

The following description preparation method provides suitable solvents, reactants, catalysts and conditions for each reaction. However, it is to be understood that these are merely illustrative in nature and are not intended to be limiting of the present invention.

(1) Preparation of Compound ($I_1$) in which $R^4$ Is Halogen

The compound ($I_1$) can be prepared by reacting a halogenating agent with compound (II) in a solvent.

Suitable solvents usable in this reaction include benzene, toluene and N,N-dimethylformamide (DMF). Suitable halogenating agents are phosphorus oxychloride and thionyl chloride. It is preferred to conduct the reaction at 20 to 150° C. for 0.5 to 10 hours, more preferably at 50 to 130° C. for 1 to 5 hours.

(2) Preparation of Compound ($I_2$) in which $R^4$ Is Substituted or Unsubstituted Phenoxy, Compounds ($I_3$) in which $R^4$ Is Substituted or Unsubstituted Phenylthio, Compound ($I_4$) in which $R^4$ Is Substituted or Unsubstituted Pyridyloxy, Compound ($I_5$) in which $R^4$Is Substituted or Unsubstituted Morpholino, or Compound ($I_6$) in which $R^4$ Is Substituted or Unsubstituted Amino The compounds ($I_2$–$I_6$) can each be prepared by reacting the corresponding compound ($I_1$) with $R^{4'}$H, in which $R^{4'}$ represents substituted or unsubstituted phenoxy, substituted or unsubstituted phenylthio, substituted or unsubstituted pyridyloxy, substituted or unsubstituted morpholino or substituted or unsubstituted amino, in the presence of a base in solvent.

Suitable bases include inorganic bases such as potassium carbonate, sodium carbonate and sodium hydride; and organic bases such as metal alkoxides. Examples of suitable solvents include DMF, dimethyl sulfoxide, acetone and methyl ethyl ketone. It is preferred to conduct the reaction at 20 to 150° C. for 1 to 20 hours, more preferably at 50 to 130° C. for 2 to 10 hours.

(3) Preparation of Compound ($I_7$) in which $R^4$ Is Substituted or Unsubstituted Aryl Compound ($I_7$) can be prepared by dissolving the corresponding compound ($I_1$) in a solvent, successively adding a palladium catalyst and an arylmagnesium bromide, and then reacting them.

Suitable solvents for this reaction include diethyl ether, tetrahydrofuran (THF), dimethoxyethane, benzene and toluene. Examples of the palladium catalyst include palladium chloride and tetrakis(triphenylphosphine)palladium. It is preferred to conduct the reaction at 20 to 100° C. for 0.5 to 2 hours, more preferably at 40 to 80° C. for 1 to 1.5 hours.

(4) Preparation of Compound ($I_8$) in which $R^4$ Is Alkylthio

Compound ($I_8$) can be prepared by reacting an alkyl halide with the corresponding compound (III) in the presence of sodium hydride in a solvent.

Suitable solvent for this reaction include DMF, dimethyl sulfoxide, acetone, THF, dioxane and methyl ethyl ketone. It is preferred to conduct the reaction under stirring at 0 to 50° C. for 0.5 to 2 hours, more preferably at 5 to 20° C. for 1 hour.

(5) Preparation of Compound ($I_9$) in which $R^4$ Is Alkylsulfonyl

Compound ($I_9$) can be prepared by oxidizing the corresponding compound ($I_8$) in a solvent.

Suitable oxidizing agents include osmium tetraoxide-sodium periodate or methachloroperbenzoic acid. As the solvent, chloroform, acetone, butanol or the like or a mixed solvent thereof can be used. It is preferred to conduct the reaction under stirring at −40 to 50° C. for 1 to 40 hours, more preferably at −10 to 20° C. for 10 to 30 hours.

(6) Preparation of Compound ($I_{10}$) in which $R^4$ is Alkylsulfonyloxy

Compound ($I_{10}$) can be prepared by reacting the corresponding compound (II) with an alkylsulfonyl chloride in a solvent.

Suitable solvents include pyridine, picoline and lutidine. It is preferred to conduct the reaction at 10 to 40° C. for 1 to 10 days, more preferably at 20 to 30° C. for 3 to 5 days.

(7) Preparation of Compound ($I_{11}$) in which $R^4$ Is Hydrogen

Compound ($I_{11}$) can be prepared by subjecting the corresponding compound ($I_1$) to catalytic reduction in the presence of a catalyst in a solvent.

Suitable solvents include methanol, ethanol, THF, ethyl acetate and acetic acid. As the catalyst, 10% palladium on charcoal can be used. It is preferred to conduct the reaction under a hydrogen gas stream at room temperature under atmospheric pressure for 1 to 10 hours, more preferably for 4 to 5 hours.

(8) Preparation of Compound ($I_{12}$) in which $R^4$ Is Hydrogen, Namely, of Pyridazine 1-oxide Compound Compound ($I_{12}$) can be prepared by reacting the corresponding compound ($I_{11}$) with hydrogen peroxide solution in a solvent.

A suitable solvent is acetic acid. It is preferred to conduct the reaction at 20 to 80° C. for 2 to 10 hours, more preferably at 40 to 60° C. for 4 to 6 hours.

(9) Preparation of Compound ($I_{13}$) in which $R^4$ Is Cyano

Compound ($I_{13}$) can be prepared by reacting the corresponding compound ($I_{12}$) with an acylating agent and an alkali cyanide in a solvent.

Suitable alkali cyanides include sodium cyanide and potassium cyanide. As the acylating agent, acetic anhydride, acetyl chloride, benzoyl chloride or the like can be used. It is preferred to conduct the reaction at 10 to 40° C. for 10 to 40 hours, more preferably at 20 to 30° C. for 20 to 30 hours.

(10) Preparation of Compound ($I_{14}$) in which $R^4$ Is Carboxyl

Compound ($I_{14}$) can be prepared by hydrolyzing the corresponding compound ($I_{13}$) in the presence of an inorganic acid or an alkali in a solvent.

Suitable solvents include water, ethanol, methanol, and mixed solvents thereof. As the inorganic acid, hydrochloric acid, sulfuric acid, nitric acid or the like can be used. As the alkali, sodium hydroxide, potassium hydroxide or the like can be used. It is preferred to conduct the reaction under stirring at 60 to 140° C. for 0.5 to 2 hours, more preferably at 80 to 120° C.

(11) Preparation of Compound ($I_{15}$) in which $R^4$ Is —$COR^5$

Compound ($I_{15}$) can be prepared by reacting a compound, which is represented by the formula $R^5$H in which $R^5$ has the same meaning as defined above, with the corresponding compound ($I_{14}$) in the presence of a condensing agent.

Suitable condensing agents include a 50% solution of cyclic 1-propanephosphoric anhydride (n=3) in ethyl acetate. As the solvent, THF, DMF or a mixed solvent thereof can be used. It is preferred to conduct the reaction under stirring at 10 to 40° C. for 1 to 7 hours, more preferably at 20 to 30° C. for 3 to 5 hours.

(12) Preparation of Compound ($I_{16}$) in which $R^4$ Is Alkenyl

Compound ($I_{16}$) can be prepared by reacting an alkenyl-magnesium bromide with the corresponding compound ($I_1$) in the presence of a palladium catalyst in a solvent under an inert gas atmosphere.

Suitable solvents include THF, benzene and toluene. As the palladium catalyst, palladium chloride, tetrakis(triphenylphosphine)palladium or the like are preferred. It is preferred to conduct the reaction at −20 to 40° C. for 0.5 to 4 hours, more preferably at −10 to 10° C. for 0.5 to 1.5 hours, followed by further reaction at 20 to 30° C. for 1 to 3 hours.

(13) Preparation of Compound ($I_{17}$) in which $R^4$ Is Hydroxyalkyl

Compounds ($I_{17}$) can be prepared by subjecting the alkenyl group of the corresponding compound ($I_{16}$) to a hydroboration reaction.

The hydroboration reaction can be conducted, for example, by adding a solution of 9-borabicyclo[3.3.1]nonane (9-BBN) or a salt thereof to a solvent, in which the compound ($I_{16}$) is contained, under an atmosphere of an inert gas, such as argon or nitrogen, stirring the resulting mixture at 10 to 40° C. for 5 to 30 hours, preferably at 20 to 30° C. for 10 to 20 hours, successively adding water, an aqueous solution of an alkali and hydrogen peroxide solution to the reaction mixture while cooling it with ice water, and then stirring the thus-obtained mixture at 10 to 40° C. for 1 to 4 hours, preferably at 20 to 30° C. for 1.5 to 3 hours.

(14) Preparation of Compound ($I_{18}$) in which $R^4$ Is Carboxyalkyl

Compound ($I_{18}$) can be prepared by subjecting the compound ($I_{17}$) to an oxidation reaction with an oxidizing agent in a solvent.

Suitable solvents include acetone and acetic acid. As the oxidizing agent, Jones reagent is preferred. It is preferred to conduct the reaction at 10 to 40° C. for 4 to 12 hours, more preferably at 20 to 30° C. for 6 to 10 hours.

(15) Preparation of Compound ($I_{19}$) in which $R^4$ Is Alkyl Substituted by Substituted or Unsubstituted Aminocarbonyl Compound ($I_{19}$) can be prepared by reacting the corresponding compound ($I_{18}$) and a compound represented by $R^6R^7NH$, in which $R^6$ and $R^7$ have the same meanings as defined above, in the same manner as in the preparation of the compound ($I_{15}$).

(Preparation Process 2)

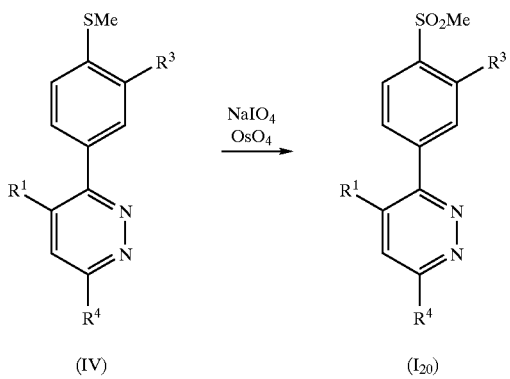

Preparation of Compound ($I_{20}$) in which $R^2$ Is Lower Alkylsulfonyl

Compound ($I_{20}$) can be prepared by oxidizing the corresponding compound (IV) in a solvent.

As this reaction, a reaction similar to that employed in the preparation of compound ($I_9$) can be used. Alternatively, hydrogen peroxide or the like can be used as the oxidizing agent, and acetic acid or the like can be used as the solvent. In this case, it is preferred to conduct the reaction at 40 to 100° C. for 0.5 to 6 hours, more preferably at 60 to 80° C. for 2 to 4 hours.

(Preparation Process 3)

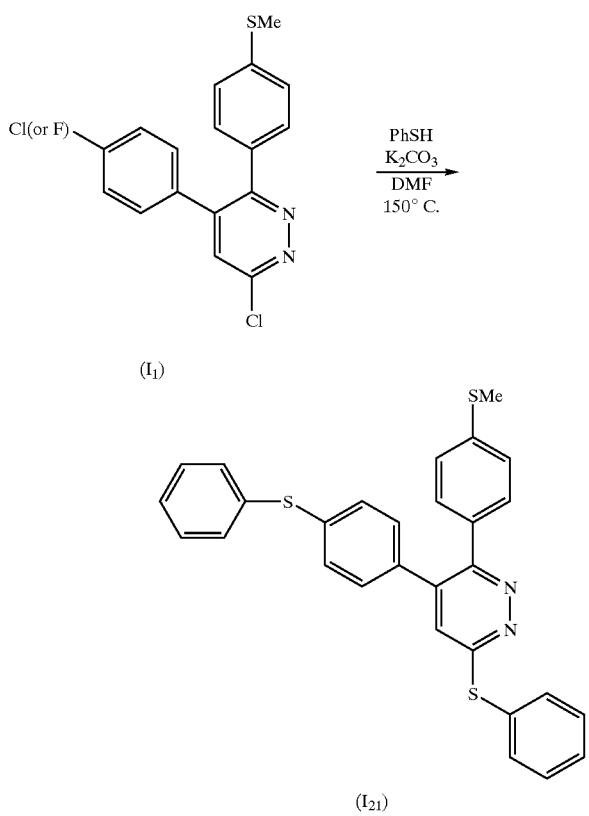

Preparation of Compound ($I_{21}$) in which $R^1$ Is Phenylthiophenyl and $R^4$ Is Phenylthio Compound ($I_{21}$) can be prepared by reacting a corresponding compound ($I_1$), in which $R^1$ is a halophenyl group, with thiophenol in the presence of a base in a solvent.

Suitable bases include inorganic bases such as potassium carbonate, sodium carbonate and sodium hydride; and organic bases such as metal alkoxides. As the solvent, DMF, dimethyl sulfoxide, acetone, methyl ethyl ketone or the like can be used. It is preferred to conduct the reaction at 50 to 300° C. for 5 to 40 hours, more preferably at 100 to 200° C. for 10 to 30 hours.

(Preparation Process 4)

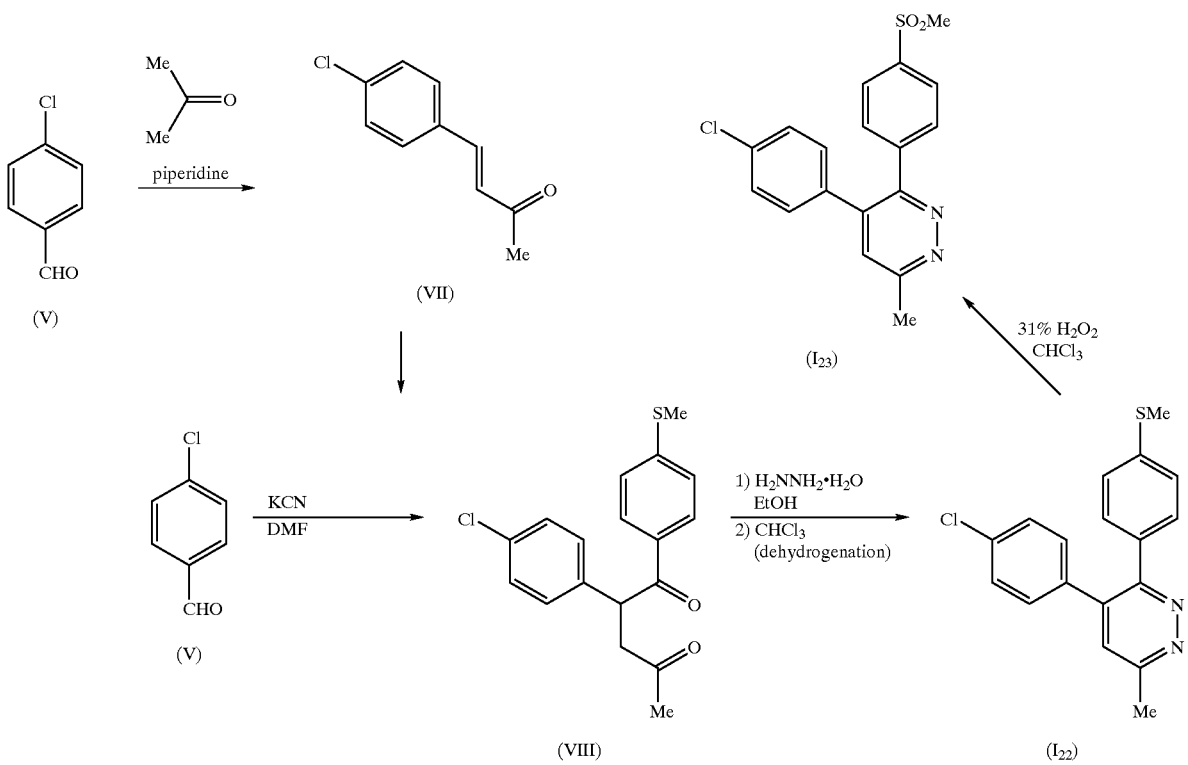

In the preparation process 4, compound (VII) can be prepared by reacting acetone with the compound (V) in the presence of a base in a solvent.

Suitable solvents include acetone, ethanol, methanol, and mixed solvents thereof Examples of the base include piperidine, morpholine and diisopropylamine. It is preferred to conduct the reaction with stirring at 10 to 40° C. for 10 minutes to 1 hour, more preferably for 20 to 40 minutes. Alternatively, as compound (VII), the commercial product available from Lancaster can also be used.

(1) Preparation of Compound ($I_{22}$) in which $R^4$ Is Alkyl

Compound ($I_{22}$) can be prepared by reacting compound (VI) and compound (VII) in the presence of an alkali cyanide in a solvent to obtain compound (VIII), reacting hydrazine hydrate with compound (VIII) in a solvent, and then conducting dehydrogenation.

Suitable solvents for the reaction between compound (VI) and compound (VII) include DMF and dimethylsulfoxide, and examples of the alkali cyanide include potassium cyanide and sodium cyanide.

Suitable solvents for the reaction with hydrazine hydrate include ethanol and isopropanol.

It is preferred to conduct the reaction under stirring at 50 to 100° C. for 4 to 10 hours, more preferably at 70 to 90° C. for 6 to 8 hours. The dehydrogenation reaction can be conducted by air oxidation in a solvent such as chloroform.

(2) Preparation of Compound ($I_{23}$) in which $R^2$ Is Alkylsulfonyl and $R^4$ Is Alkyl Compound ($I_{23}$) can be prepared by reacting a corresponding compound ($I_{22}$), in which $R^2$ is alkylthio, in a similar manner as in the preparation of compound ($I_{20}$).

(Preparation Process 5)

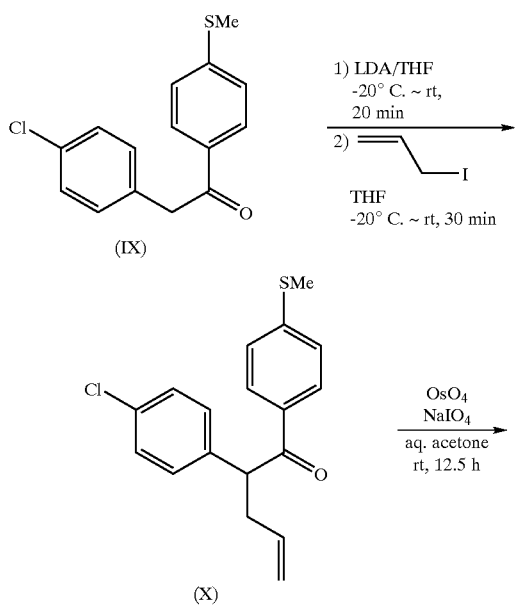

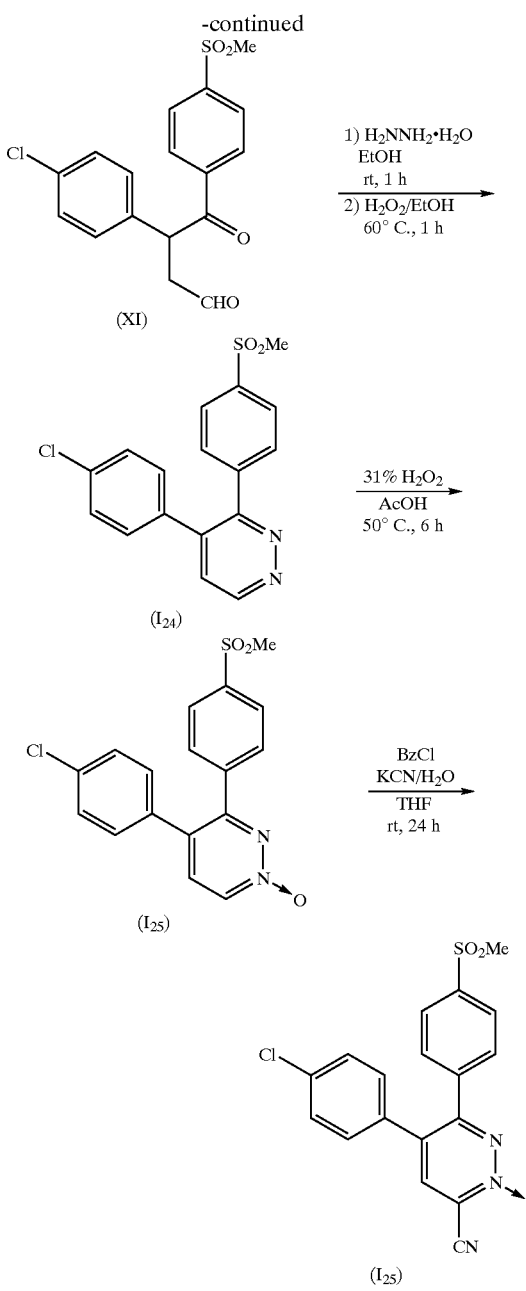

In preparation process 5, compound (IX) can be prepared by a known process (WO 9925697). Compound (X) can be obtained by adding lithium diisopropylamide (LDA) at −20° C. to a solution of compound (IX) in THF, reacting them at room temperature for 20 minutes, adding allyl iodide and then reacting them at room temperature for 30 minutes. Compound (XI) can be prepared by oxidizing compound (X) with osmium tetraoxide, similar to the procedure discussed earlier.

(1) Preparation of Compound ($I_{24}$) in which $R^1$ Is Halophenyl and $R^4$ Is Hydrogen Compound ($I_{24}$) can be prepared by reacting compound (XI) in a similar manner as in the preparation of compound ($I_{22}$).

(2) Preparation of Compound, Pyridazine 1-oxide, ($I_{25}$) in which $R^1$ Is Halophenyl and $R^4$ Is Hydrogen Compound ($I_{25}$) can be prepared by reacting compound ($I_{24}$) in a similar manner as in the preparation of compound ($I_{12}$).

(3) Preparation of Compound ($I_{26}$) in which $R^1$ Is Halophenyl and $R^4$ Is Cyano Compound ($I_{26}$) can be prepared by reacting compound ($I_{25}$) in a similar manner as in the preparation of compound ($I_{13}$).

The intermediates and target compounds obtained in the above-described individual reactions can be separated and purified by purification methods commonly employed in synthetic organic chemistry, including, but not limited to, filtration, extraction, washing, drying, concentration, recrystallization, various chromatographic methods. The intermediates may be provided for the next reactions without purifying them or can be purified as desired, using conventional purification methods. Further, they may also be obtained as solvates of solvents such as reaction solvents or recrystallization solvents, especially as hydrates.

Examples of the salt of the phenylpyridazine compound of the present invention, are the hydrochloride, nitrate, hydrobromide, acetate, sulfate, p-toluenesulfonate, methanesulfonate, fumarate, succinate, lactate, sodium salt, potassium salt, magnesium salt, calcium salt, ammonium salt, methylammonium salt, dimethylammonium salt, and trimethylammonium.

The phenylpyridazine compounds (I) and their salts according to the present invention, have excellent inhibitory activity against interleukin-1β production, and are useful for the prevention and treatment of diseases caused by stimulation of interleukin-1β production. Many diseases are caused by this stimulation of interleukin-1β production, such as immune system diseases, inflammatory diseases, ischemic diseases, osteoporosis and ichoremia. The present compounds or salts are particularly useful as medicines such as preventives and therapeutics for rheumatism, immune deficiency syndrome, arthritis, inflammatory colitis, ischemic heart diseases, ischemic encephalopathy, ischemic nephritis, ischemic hepatitis, insulin-dependent diabetes mellitus, arterial sclerosis, Parkinson's disease and Alzbeimer's disease, and leukemia or as interleukin-1β production inhibitors.

Pharmaceutical compositions according to the present invention contain the phenylpyridazine compounds (I) or its salt as an active ingredient. Any administration route can be used for the composition, including but not limited to, oral administration by tablets, capsules, granules, powders or syrups and parenteral administration by intravenous injections, intramuscular injections, suppositories, inhalants, transdermal preparations, eye drops or nasal drops. Upon formulation of pharmaceutical compositions of these various unit dosage forms, the active ingredients can be used alone or in combination with conventional pharmaceutically acceptable excipients, binders, extenders, disintegrators, surfactants, lubricants, dispersants, buffers, preservatives, corrigents, perfumes, coating agents, vehicles, diluents and/or carriers as desired.

The dosage of each pharmaceutical composition according to the present invention varies depending on the body weight, age, sex and condition of the patient. In the case of an adult, however, it is generally preferred to orally or parenterally administer the compound represented by the formula (I) in an amount of from about 0.01 to 1,000 mg, preferably 0.1 to 100 mg per day at once or in several portions. If administered in several portions, the several portions can be equal to one another or vary depending on the time between doses, in order to account for the active lifetime of the present compounds in the body.

Having generally described this invention, a further understanding can be obtained by reference to certain specific examples which are provided herein for purposes of illustration only and are not intended to be limiting unless otherwise specified.

EXAMPLES

Example 1

Preparation of 3,4-bis(4-methoxyphenyl)-6-phenylpyridazine 3,4-Bis(4-methoxyphenyl)-6-chloropyridazine [Eur. J. Med. Chem.-Chimica Therapeutica, 14, 53–60 (1979)] (309.3 mg, 0.95 mmol) was dissolved in benzene (2 ml). Tetrakis(triphenylphosphine)palladium [Pd(Ph$_3$P)$_4$] (90.6 mg, 0.08 mmol) and phenylmagnesium bromide (1.0 M tetrahydrofuran solution) (1.5 ml) were then added successively, followed by stirring at 60° C. for 75 minutes. After water-methylene chloride was added to the reaction mixture, the mixture was extracted with methylene chloride and the organic layer was dried over anhydrous sodium sulfate. The solvent was distilled off and the residue was then separated and purified by chromatography on a silica gel column [silica gel (40 g), hexane/ethyl acetate (2/1)], whereby the title compound was obtained as a pale yellow amorphous solid (129 mg, 36.9%)

$^1$H-NMR (CDCl$_3$) δ: 3.83(3H,s), 3.84(3H,s), 6.86(2H,d, J=9.04 Hz), 6.90(2H,d,J=9.04 Hz), 7.22(2H,d,J=9.04 Hz), 7.45–7.55(5H,m), 7.79(1H,s), 8.15–8.20(2H,m).

IR (film) cm$^{-1}$: 1609,1514,1392,1252,1178.

Example 2

Preparation of 3,4-bis(4-methoxyphenyl)-6-(2,4-difluorophenylthio)pyridazine 3,4-Bis(4-methoxyphenyl)-6-chloropyridazine (440 mg, 1.35 mmol) was dissolved in N,N-dimethylformamide (5 ml). Potassium carbonate (400 mg, 2.90 mmol) and 2,4-difluorothiophenol (300 mg, 2.05 mmol) were then added successively, followed by stirring at 80° C. for 7 hours. The reaction mixture was concentrated under reduced pressure, the residue was extracted with chloroform, and the organic layer was dried over anhydrous sodium sulfate. The solvent was distilled off, the residue was separated and purified by preparative thin-layer chromatography on a silica gel [developing solvent: hexane/ethyl acetate (8/1)], and the resulting crystals were recrystallized from chloroform-diethyl ether-hexane, whereby colorless needles were obtained (219.7 mg, 37.4%). Melting point: 112.0–113.0° C.

$^1$H-NMR (CDCl$_3$) δ: 3.80(3H,s), 3.81(3H,s), 6.80(2H,d, J=8.79 Hz), 6.83(2H,d,J=8.79 Hz), 6.95–7.02(3H,m), 7.08 (2H,d,J=8.79 Hz), 7.36(2H,d,J=8.79 Hz), 7.70(1H,ddd,J= 1.71,6.35,8.79 Hz).

IR (KBr) cm$^{-1}$: 1608,1509,1487,1387,1297,1251,1178.

Example 3

Preparation of 3,4-bis(4-methoxyphenyl)-6-(phenoxy)pyridazine

In a similar manner as in Example 2, 3,4-bis(4-methoxyphenyl)-6-chloropyridazine (160 mg, 0.490 mmol) and phenol were reacted as starting materials at 120° C. for 22 hours and post-treatment was then conducted, whereby the title compound was obtained as colorless needles (133.1 mg, 70.7%). Melting point: 198.8–199.5° C. (ethyl acetate-hexane).

$^1$H-NMR (CDCl$_3$) δ: 3.81(3H,s), 3.83(3H,s), 6.81(2H,d, J=9.04 Hz), 6.85(2H,d J=8.79 Hz), 7.09(1H,s), 7.15(2H,d, J=8.79 Hz), 7.21–7.31(3H,m), 7.34(2H,d,J=9.04 Hz), 7.35–7.46(2H,m).

IR (KBr) cm$^{-1}$: 1608,1512,1489,1419,1397,1251,1216, 1174.

Example 4

Preparation of 3,4-bis(4-methoxyphenyl)-6-(phenylthio)pyridazine

In a similar manner as in Example 2, 3,4-bis(4-methoxyphenyl)-6-chloropyridazine (352.5 mg, 1.08 mmol) and thiophenol were reacted as starting materials at 100° C. for 7 hours and post-treatment was then conducted, whereby the title compound was obtained as a colorless crystalline powder (55.8 mg, 12.9%). Melting point: 176.9–177.8° C. (chloroform-diethyl ether)

$^1$H-NMR (CDCl$_3$) δ: 3.79(3H,s), 3.80(3H,s), 6.80(2H,d, J=8.79 Hz), 6.81(2H,d,J=8.79 Hz), 7.00(2H,d,J=8.79 Hz), 7.02(1H,s), 7.34(2H,d,J=8.79 Hz), 7.42–7.46(3H,m), 7.65–7.69(2H,m).

IR (KBr) cm$^{-1}$: 1607,1508,1387,1219,1174.

Example 5

Preparation of 3,4-bis(4-methoxyphenyl)-6-(2,3-difluorophenoxy)pyridazine

In a similar manner as in Example 2, 3,4-bis(4-methoxyphenyl)-6-chloropyridazine (180 mg, 0.551 mmol) and 2,3-difluorophenol were reacted as starting materials at 150° C. for 19 hours and post-treatment was then conducted, whereby the title compound was obtained as a colorless crystalline powder (203.3 mg, 90.0%). Melting point: 157.5–159.0° C. (chloroform-hexane).

$^1$H-NMR (CDCl$_3$) δ: 3.80(3H,s), 3.83(3H,s), 6.81(2H,d, J=8.79 Hz), 6.88(2H,d,J=8.79 Hz), 7.07–7.17(3H,m), 7.18 (1H,d,J=8.79 Hz), 7.22(1H,s), 7.34(2H,d,J=8.79 Hz).

IR (KBr) cm$^{-1}$: 1609,1513,1478 1420,1396,1372,1295, 1251, 1201,1176.

Example 6

Preparation of 3,4-bis(4-methoxyphenyl)-6-(2,4-difluorophenoxy)pyridazine

In a similar manner as in Example 2, 3,4-bis(4-methoxyphenyl)-6-chloropyridazine (200 mg, 0.613 mmol) and 2,4-difluorophenol were reacted as starting materials at 120° C. for 13 hours and post-treatment was then conducted, whereby the title compound was obtained as a colorless crystalline powder (136 mg, 52.5%). Melting point: 141.7–142.5° C. (diethyl ether-hexane).

$^1$H-NMR (CDCl$_3$) δ: 3.80(3H,s), 3.83(3H,s), 6.80(2H,d, J=8.79 Hz), 6.87(2H,d,J=8.79 Hz), 6.90–7.02(2H,m), 7.17 (2H,d,J=8.79 Hz), 7.19(1H,s), 7.32(1H,m), 7.33(2H,d,J= 8.79 Hz).

IR (KBr) cm$^{-1}$: 1610,1506,1395,1299,1249,1208,1179.

Example 7

Preparation of 3,4-bis(4-methoxyphenyl)-6-(2,5-difluorophenoxy)pyridazine

In a similar manner as in Example 2, 3,4-bis(4-methoxyphenyl)-6-chloropyridazine (200 mg, 0.613 mmol) and 2,5-difluorophenol were reacted as starting materials at 150° C. for 24 hours and post-treatment was then conducted, whereby the title compound was obtained as a colorless crystalline powder (235.5 mg, 91.5%). Melting point: 174.4–175.2° C. (chloroform-hexane).

$^1$H-NMR (CDCl$_3$) δ: 3.80(3H,s), 3.83(3H,s), 6.81(2H,d, J=8.79 Hz), 6.87(2H,d,J=8.79 Hz), 6.94(1H,m), 7.09–7.17 (2H,m), 7.18(2H,d,J=8.79 Hz), 7.20(1H,s), 7.34(2H,d,J=8.79 Hz).

IR (KBr) cm$^{-1}$: 1608,1507,1419,1398,1372,1301,1250, 1209, 1173.

Example 8

Preparation of 3,4-bis(4-methoxyphenyl)-6-(2,6-difluorophenoxy)pyridazine

In a similar manner as in Example 2, 3,4-bis(4-methoxyphenyl)-6-chloropyridazine (200 mg, 0.613 mmol) and 2,6-difluorophenol were reacted as starting materials at 150° C. for 72 hours and post-treatment was then conducted, whereby the title compound was obtained as a colorless crystalline powder (101.0 mg, 39.3%). Melting point: 204.7–206.4° C. (chloroform-hexane).

$^1$H-NMR (CDCl$_3$) δ: 3.80(3H,s), 3.83(3H,s), 6.80(2H,d, J=8.79 Hz), 6.87(2H,d,J=8.79 Hz), 7.03(2H,t,J=7.57 Hz), 7.18(1H,m), 7.19(2H,d,J=8.79 Hz), 7.27(1H,s), 7.33(2H, d!J=8.79 Hz).

IR (KBr) cm$^{-1}$: 1609,1513,1499,1479,1394,1295,1251, 1221, 1178.

Example 9

Preparation of 3,4-bis(4-methoxyphenyl)-6-(3,4-difluorophenoxy)pyridazine

In a similar manner as in Example 2, 3,4-bis(4-methoxyphenyl)-6-chloropyridazine (150 mg, 0.459 mmol) and 3,4-difluorophenol were reacted as starting materials at 150° C. for 14 hours and post-treatment was then conducted, whereby the title compound was obtained as a pale yellow amorphous solid (190.2 mg, 99.1%).

$^1$H-NMR (CDCl$_3$) δ: 3.81(3H,s), 3.83(3H,s), 6.81(2H,d, J=8.79 Hz), 6.86(2H,d,J=8.79 Hz), 7.05(1H,m), 7.11–7.23 (5H,m), 7.33(2H,d,J=8.79 Hz).

IR (KBr) cm$^{-1}$: 1610,1587,1574,1506,1419,1394,1373, 1298, 1251,1209,1179.

Example 10

Preparation of 3,4-bis(4-methoxyphenyl)-6-(3,5-difluorophenoxy)pyridazine

In a similar manner as in Example 2, 3,4-bis(4-methoxyphenyl)-6-chloropyridazine (250 mg, 0.766 mmol) and 3,5-difluorophenol were reacted as starting materials at 150° C. for 6 hours and post-treatment was then conducted, whereby the title compound was obtained as colorless needles (315.0 mg, 98.0%). Melting point: 135.1–137.5° C. (ethyl acetate-diethyl ether-hexane).

$^1$H-NMR (CDCl$_3$) δ: 3.81(3H,s), 3.83(3H,s), 6.70(1H,tt, J=1.20,9.03 Hz), 6.80–6.90(6H,m), 7.15(1H,s), 7.16(2H,d, J=8.79 Hz), 7.35(2H,d,J=8.79 Hz).

IR (KBr) cm$^{-1}$: 1609,1514,1466,1394,1373,1253,1212, 1182.

Example 11

Preparation of 3,4-bis(4-methoxyphenyl)-6-(2,3,5,6-tetrafluorophenoxy)pyridazine In a similar manner as in Example 2, 3,4-bis(4-methoxyphenyl)-6-chloropyridazine (200 mg, 0.613 mmol) and 2,3,5,6-tetrafluorophenol were reacted as starting materials at 150° C. for 12 hours and post-treatment was then conducted, whereby the title compound was obtained as a colorless crystalline powder (105.7 mg, 37.8%). Melting point: 172.5–174.5° C. (hexane).

$^1$H-NMR (CDCl$_3$) δ: 3.81(3H,s), 3.84(3H,s), 6.82(2H,d, J=8.79 Hz), 6.88(2H,d,J=8.79 Hz), 7.03(1H,tt,J=7.08,10.01 Hz), 7.19(2H,d,J=8.79 Hz), 7.31(1H,s) 7.34(2H,d,J=8.79 Hz).

IR (KBr) cm$^{-1}$: 1610,1526,1515,1484,1393,1264,1250, 1203, 1181.

Example 12

Preparation of 3,4-bis(4-methoxyphenyl)-6(2,3,4,5,6-pentafluorophenoxy)pyridazine In a similar manner as in Example 2, 3,4-bis(4-methoxyphenyl)-6-chloropyridazine (200 mg, 0.613 mmol) and 2,3,4,5,6-pentafluorophenol were reacted as starting materials at 150° C. for 24 hours and post-treatment was then conducted, whereby the title compound was obtained as a colorless amorphous solid (175.6 mg, 60.5%).

$^1$H-NMR (CDCl$_3$) δ: 3.81(3H,s), 3.84(3H,s), 6.82(2H,d, J=8.79 Hz), 6.88(2H,d,J=8.79 Hz), 7.19(2H,d,J=8.79 Hz), 7.31(1H,s), 7.33(2H,d,J=8.79 Hz).

IR (film) cm$^{-1}$: 1610,1520,1472,1395,1371,1298,1253, 1205,1180.

Example 13

Preparation of 3,4-bis(4-methoxyphenyl)-6-(2,4-dichlorophenoxy)pyridazine

In a similar manner as in Example 2, 3,4-bis(4-methoxyphenyl)-6-chloropyridazine (150 mg, 0.495 mmol) and 2,4-dichlorophenol were reacted as starting materials at 150° C. for 15 hours and post-treatment was then conducted, whereby the title compound was obtained as a colorless crystalline powder (195.5 mg, 93.9%). Melting point: 152.2–152.8° C. (ethyl acetate-hexane).

$^1$H-NMR (CDCl$_3$) δ: 3.80(3H,s), 3.83(3H,s), 6.80(2H,d, J=8.79 Hz), 6.87(2H,d,J=8.79 Hz), 7.18(2H,d,J=8.79 Hz), 7.20(1H,s), 7.29–7.33(2H,m), 7.34(2H,d,J=8.79 Hz), 7.51 (1H,d,J=1.71 Hz).

IR (KBr) cm$^{-1}$: 1608,1513,1473,1420,1394,1372,1255, 1231,1179.

Example 14

Preparation of 3,4-bis(4-methoxyphenyl)-6-(3,4,5-trichlorophenylthio)pyridazine

In a similar manner as in Example 2, 3,4-bis(4-methoxyphenyl)-6-chloropyridazine (200 mg, 0.613 mmol) and 3,4,5-trichlorothiophenol [Ger. Offen. DE 2515699 19751023 (Dow Chemical Co., U.S.A.)] were reacted as starting materials at 100° C. for 72 hours and post-treatment was then conducted, whereby the title compound was obtained as a colorless amorphous solid (125.3 mg, 40.6%)

$^1$H-NMR (CDCl$_3$) δ: 3.79(3H,s), 3.81(3H,s), 6.81(2H,d, J=8.79 Hz), 6.84(2H,d,J=8.79 Hz), 7.10(2H,d,J=8.79 Hz), 7.27(1H,s), 7.36(2H,d,J=8.79 Hz), 7.68(2H,s).

IR (film) cm$^{-1}$: 1608,1510,1385,1298,1252,1179.

Example 15

Preparation of 3,4-bis(4-methoxyphenyl)-6-(4-methoxyphenoxy)pyridazine

In a similar manner as in Example 2, 3,4-bis(4-methoxyphenyl)-6-chloropyridazine (150 mg, 0.495 mmol)

and 4-methoxyphenol were reacted as starting materials at 150° C. for 24 hours and post-treatment was then conducted, whereby the title compound was obtained as colorless prisms (180.1 mg, 94.7%). Melting point: 146.7–148.2° C. (ethyl acetate-diethyl ether-hexane).

$^1$H-NMR (CDCl$_3$) δ: 3.80(3H,s), 3.82(3H,s), 3.83(3H,s), 6.80(2H,d,J=9.03 Hz), 6.85(2H,d,J=9.03 Hz), 6.94(2H,d,J=9.03 Hz), 7.05(1H,s), 7.13(2H,d,J=9.03 Hz), 7.20(2H,d,J=9.03 Hz), 7.33(2H,d,J=9.03 Hz).

IR (KBr) cm$^{-1}$: 1610,1512,1504,1396,1252,1219,1180.

Example 16

Preparation of 3,4-bis(4-methoxyphenyl)-6-(3-nitrophenoxy)pyridazine

In a similar manner as in Example 2, 3,4-bis(4-methoxyphenyl)-6-chloropyridazine (106.9 mg, 0.327 mmol) and 3-nitrophenol were reacted as starting materials at 150° C. for 17 hours and post-treatment was then conducted, whereby the title compound was obtained as pale yellow prisms (140.4 mg, 99.9%). Melting point: 172.2–174.0° C. (ethyl acetate-diethyl ether-hexane).

$^1$H-NMR (CDCl$_3$) δ3.81(3H,s), 3.84(3H,s), 6.82(2H,d,J=8.79 Hz), 6.89(2H,d,J=8.79 Hz), 7.18(2H,d,J=8.79 Hz), 7.21 (1H,s), 7.34(2H,d,J=8.79 Hz), 7.60(1H,dd,J=7.82,8.30 Hz), 7.67(1H,ddd,J=1.22,2.20,8.30 Hz), 8.12(1H,ddd,J=1.22,1.95,7.82 Hz), 8.17(1H,dd,J=1.95,2.20 Hz).

IR (KBr) cm$^{-1}$: 1610,1528,1514,1395 1347,1253,1227, 1178.

Example 17

Preparation of 3,4-bis(4-methoxyphenyl)-6-(4-nitrophenoxy)pyridazine

In a similar manner as in Example 2, 3,4-bis(4-methoxyphenyl)-6-chloropyridazine (150 mg, 0.495 mmol) and 4-nitrophenol were reacted as starting materials at 150° C. for 15 hours and post-treatment was then conducted, whereby the title compound was obtained as a pale yellow crystalline powder (146.1 mg, 74.1%). Melting point: 197.7–201.1° C. (ethyl acetate-hexane).

$^1$H-NMR (CDCl$_3$) δ: 3.81(3H,s), 3.83(3H,s), 6.81(2H,d, J=8.79 Hz), 6.85(2H,d,J=8.79 Hz), 7.03(1H,s), 7.11(2H,d, J=8.79 Hz), 7.19(2H,d,J=8.79 Hz), 8.09(2H,d,J=9.04 Hz), 8.34(2H,d,J=9.04 Hz).

IR (KBr) cm$^{-1}$: 1675,1608,1590,1515,1488,1345,1296, 1250, 1181.

Example 18

Preparation of 3,4-bis(4-methoxyphenyl)-6-(2-cyanophenoxy)pyridazine

In a similar manner as in Example 2, 3,4-bis(4-methoxyphenyl)-6-chloropyridazine (110 mg, 0.337 mmol) and 2-cyanophenol were reacted as starting materials at 150° C. for 24 hours and post-treatment was then conducted, whereby the title compound was obtained as a pale yellow amorphous solid (121.4 mg, 88.1%). Melting point: 197.7–201.1° C. (ethyl acetate-hexane).

$^1$H-NMR (CDCl$_3$) δ: 3.81(3H,s), 3.84(3H,s), 6.82(2H,d, J=8.79 Hz), 6.88(2H,d,J=8.79 Hz), 7.19(2H,d,J=8.79 Hz), 7.29(1H,s), 7.34(2H,d,J=8.79 Hz), 7.35(1H,ddd,J=1.71 7.51,8.79 Hz), 7.54(1H,dd,J=0.98,8.79 Hz), 7.67(1H,ddd,J=1.22,7.51,8.79 Hz), 7.73(1H,dd,J=1.22,7.32 Hz).

IR (KBr) cm$^{-1}$: 3233,1609,1514,1486,1395,1252,1235, 1179.

Example 19

Preparation of 3,4-bis(4-methoxyphenyl)-6-(3-cyanophenoxy)pyridazine

In a similar manner as in Example 2, 3,4-bis(4-methoxyphenyl)-6-chloropyridazine (175 mg, 0.536 mmol) and 3-cyanophenol were reacted as starting materials at 150° C. for 19 hours and post-treatment was then conducted, whereby the title compound was obtained as colorless prisms (165 mg, 75.2%). Melting point: 169.9–172.7° C. (ethyl acetate-diethyl ether-hexane).

$^1$H-NMR (CDCl$_3$) δ: 3.81(3H,s), 3.83(3H,s), 6.82(2H,d, J=8.79 Hz), 6.88(2H,d,J=8.79 Hz), 7.17(2H,d,J=8.79 Hz), 7.18(1H,s) 7.34(2H,d,J=8.79 Hz), 7.52–7.61(4H,m).

IR (KBr) cm$^{-1}$: 2236,1608,1514,1391,1255,1242,1179.

Example 20

Preparation of 3,4-bis(4-methoxyphenyl)-6-(4-cyanophenoxy)pyridazine

In a similar manner as in Example 2, 3,4-bis(4-methoxyphenyl)-6-chloropyridazine (150 mg, 0.459 mmol) and 4-cyanophenol were reacted as starting materials at 150° C. for 13 hours and post-treatment was then conducted, whereby the title compound was obtained as a pale yellow crystalline powder (108.0 mg, 57.5%). Melting point: 167.3–170.5° C. (ethyl acetate-hexane).

$^1$H-NMR (CDCl$_3$) δ: 3.81(3H,s), 3.83(3H,s), 6.83(2H,d, J=8.79 Hz), 6.89(2H,d,J=8.79 Hz), 7.17(2H,d,J=8.79 Hz), 7.19(1H,s), 7.35(2H,d,J=8.79 Hz), 7.42(2H,d,J=8.55 Hz), 7.73(2H,d,J=8.55 Hz).

IR (KBr) cm$^{-1}$: 2228,1608,1584,1513,1501,1421,1394, 1372, 1298,1254,1224,1177.

Example 21

Preparation of 3,4-bis(4-methoxyphenyl)-6-(4-pyridyloxy)pyridazine

In a similar manner as in Example 2, 3,4-bis(4-methoxyphenyl)-6-chloropyridazine (200 mg, 0.613 mmol) and 4-hydroxypyridine were reacted as starting materials at 150° C. for 22 hours and post-treatment was then conducted, whereby the title compound was obtained as a pale yellow crystalline powder (201.6 mg, 85.2%). Melting point: 186.8–188.8° C. (hexane).

$^1$H-NMR (CDCl$_3$) δ: 3.84(3H,s), 3.85(3H,s), 6.58(2H,d, J=8.06 Hz), 6.87(2H,d,J=8.79 Hz), 6.90(2H,d,J=8.79 Hz), 7.20(2H,d,J=8.79 Hz), 7.42(2H,d,J=8.79 Hz), 7.49(1H,s), 8.31(2H,d,J=8.06 Hz).

IR (KBr) cm$^{-1}$: 1637,1609,1567,1514,1254,1190.

Example 22

Preparation of 6-chloro-3-(4-methoxyphenyl)-4-(4-pyridyl)pyridazine

Phosphorus oxychloride (100 ml) was added to 6-(4-methoxyphenyl)-5-(4-pyridyl)-2H-pyridazin-3-one [WO 9925697] (3.00 g, 10.8 mmol), followed by stirring at 90° C. for 1 hour. The reaction mixture was concentrated under reduced pressure, and water was added to the residue. The resulting mixture was extracted with ethyl acetate. The organic layer was washed with a saturated aqueous solution of potassium carbonate, and was then dried over anhydrous sodium sulfate. The extract was concentrated under reduced pressure and the residue was crystallized from ethyl acetate-diethyl ether, whereby the title compound was obtained as pale yellow prisms the melting point of which was 186.2–188.9° C. (2.88 g, 90.0%).

$^1$H-NMR (CDCl$_3$) δ: 3.82(3H,s), 6.85(2H,d,J=8.55 Hz), 7.15(2H,d,J=6.10 Hz), 7.33(2H,d=8.55 Hz), 7.49(1H,s), 8.64(2H,d,J=6.10 Hz). IR (KBr) cm$^{-1}$: 1608,1579,1562, 1520,1387,1254,1182.

Example 23

Preparation of 6-(2,4-difluorophenoxy)-3-(4-methoxyphenyl)-4-(4-pyridyl)pyridazine In a similar manner as in Example 2, 6-chloro-3-(4-methoxyphenyl)-4-(4-pyridyl)pyridazine (150 mg, 0.504 mmol) and 2,4-difluorophenol were reacted as starting materials at 150° C. for 25 hours and post-treatment was then conducted, whereby the title compound was obtained as a pale yellow amorphous solid (157.0 mg, 79.6%).

$^1$H-NMR (CDCl$_3$) δ: 3.80(3H,s), 6.81(2H,d,J=8.78 Hz), 6.91–7.03(2H,m), 7.18(2H,d,J=6.11 Hz), 7.24(1H,s), 7.28 (2H,d,J=8.78 Hz), 7.29(1H,m), 8.64(2H,d,J=6.11 Hz).

IR (film) cm-1: 1610,1586,1506,1399,1374,1250,1212, 1178.

Example 24

Preparation of 6-chloro-3-(4-methoxyphenyl)-4-phenylpyridazine 6-(4-Methoxyphenyl)-5-phenyl-2H-pyridazin-3-one [WO 9925697] (2.76 g, 9.60 mmol) and phosphorus oxychloride (2.8 mP) were stirred at 90° C. for 5 hours in benzene. The reaction mixture was processed in a similar manner as in Example 22, whereby the title compound was obtained as a pale yellow-brown oil (1.83 g, 64.3%)

$^1$H-NMR (CDCl$_3$) δ: 3.86(3H,s), 6.82(2H,d,J=8.79 Hz), 7.19–7.22(2H,m), 7.33–7.39(5H,m), 7.48(1H,s).

IR (film) cm$^{-1}$: 1609,1579,1558,1521,1499,1386,1337, 1298,1253,1177.

Example 25

Preparation of 6-(2,3-difluorophenoxy)-3-(4-methoxyphenyl)-4-phenylpyridazine

In a similar manner as in Example 2, 6-chloro-3-(4-methoxyphenyl)-4-phenylpyridazine (210 mg, 0.708 mmol) and 2,3-difluorophenol were reacted as starting materials at 150° C. for 20 hours and post-treatment was then conducted, whereby the title compound was obtained as colorless prisms (230.3 mg, 83.4%). Melting point: 155.2–156.6° C. (ethyl acetate-hexane).

$^1$H-NMR (CDCl$_3$) δ: 3.79(3H,s), 6.79(2H,d,J=8.8 Hz), 7.04–7.18(3H,m), 7.21–7.42(8H,m).

IR (KBr) cm$^{-1}$: 1608,1508,1478,1399,1371,1362,1255, 1224, 1207,1182,1033,1014,849.

Mass m/z: 390(M$^+$).

Example 26

Preparation of 6-(2,4-difluorophenoxy)-3-(4-methoxyphenyl)-4-phenylpyridazine

In a similar manner as in Example 2, 6-chloro-3-(4-methoxyphenyl)-4-phenylpyridazine (215 mg, 0.725 mmol) and 2,4-difluorophenol were reacted as starting materials at 150° C. for 20 hours and post-treatment was then conducted, whereby the title compound was obtained as colorless needles (169.7 mg, 60.0%). Melting point: 169.0–169.9° C. (ethyl acetate-hexane).

$^1$H-NMR (CDCl$_3$) δ: 3.79(3H,s), 6.78(2H,d,J=8.79 Hz), 6.88–7.03(2H,m), 7.19–7.42(9H,m).

IR (KBr) cm$^{-1}$: 1508,1396,1249,1213.

Mass m/z: 390(M$^+$).

Example 27

Preparation of 3-(4-methoxyphenyl)-6-(2,3,4,5,6-pentafluorophenoxy)-4-phenylpyridazine In a similar manner as in Example 2, 6-chloro-3-(4-methoxyphenyl)-4-phenylpyridazine (200 mg, 0.675 mmol) and 2,3,4,5,6-pentafluorophenol were reacted as starting materials at 150° C. for 48 hours and post-treatment was then conducted, whereby the title compound was obtained as a colorless crystalline powder (91.2 mg, 30.5%). Melting point: 133.1–133.9° C. (ethyl acetate-hexane).

$^1$H-NMR (CDCl$_3$) δ: 3.78(3H,s), 6.79(2H,d,J=8.79 Hz), 7.24–7.40(8H,m).

IR (KBr) cm$^{-1}$: 1612,1519,1399,1369,1207,1178.

Example 28

Preparation of 6-chloro-4-(4-fluorophenyl)-3-[4-(methylthio)phenyl]pyridazine 5-(4-Fluorophenyl)-6-[4-(methylthio)phenyl]-2H-pyridazin-3-one (510 mg, 1.633 mmol) [WO 9925697] and phosphorus oxychloride (8 ml) were stirred at 100° C. for 2 hours. The reaction mixture was processed in a similar manner as in Example 22. Yellow crystals so obtained were recrystallized from ethyl acetate-hexane, whereby the title compound was obtained as pale yellow needles (367 mg, 69.2%). Melting point: 130.9–131.4° C.

$^1$H-NMR (CDCl$_3$) δ: 2.49(3H,s), 7.06(2H,d,J=8.67 Hz), 7.15–7.22(4H,m), 7.32(2H,d,J=8.55 Hz), 7.49(1H,s).

IR (KBr) cm$^{-1}$: 1603,1595,1503,1385,1221,1137,1109, 843,828,784.

Mass m/z: 330(M$^+$),331(M$^+$),332(M$^+$),333(M$^+$),334(M$^+$).

Example 29

Preparation of 6-(2,4-difluorophenoxy)-4-(4-fluorophenyl)-3-[4-(methylthio)phenyl]pyridazine In a similar manner as in Example 2, 6-chloro-4-(4-fluorophenyl)-3-[4-(methylthio)phenyl]pyridazine (198 mg, 0.599 mmol) and 2,4-difluorophenol were reacted as starting materials at 150° C. for 20 hours and post-treatment was then conducted, whereby the title compound was obtained as pale yellow crystals (197 mg, 77.4%). Melting point: 140.6–143.4° C. (acetone-water).

$^1$H-NMR (CDCl$_3$) δ: 2.47(3H,s), 6.58–7.33(12H,m).

IR (KBr) cm$^{-1}$: 1638,1606,1505,1393,1213,1140,1101, 965,849.

Mass m/z: 424(M$^+$),425(M$^+$),426(M$^+$).

Example 30

Preparation of 3-[4-(methylthio)phenyl]-6-phenylthio-4-[4-(phenylthio)phenyl]pyridazine In a similar manner as in Example 2, 6-chloro-4-(4-fluorophenyl)-3-[4-(methylthio)phenyl]pyridazine (198 mg, 0.599 mmol) and thiophenol (165 mg, 1.5 mmol) were reacted as starting materials at 150° C. for 20 hours and post-treatment was then conducted, whereby the title compound was obtained as a yellow oil (217 mg, 73.1%).

$^1$H-NMR (CDCl$_3$) δ: 2.47(3H,s), 6.95–7.02(3H,m), 7.10–7.16(4H,m), 7.29–7.46(10H,m), 7.65–7.68(2H,m).

IR (KBr) cm$^{-1}$: 1674,1594,1475,1439,1379,1336,1106, 824.

Mass m/z: 494(M$^+$),496(M$^+$).

Example 31

Preparation of 6-chloro-4-(4-chlorophenyl)-3-[4-(methylthio)phenyl]pyridazine 5-(4-Chlorophenyl)-6-[4-(methylthio)phenyl]-2H-pyridazin-3-one [WO 9925697] (700 mg) was reacted as a starting material at 100° C. for 2 hours in a similar manner as in Example 22, whereby the title compound was obtained in a yield of 93.4% as colorless crystals (dichloromethane-hexane). Melting point: 145.0–145.8° C.

$^1$H-NMR (CDCl$_3$) δ: 2.49(3H,s), 7.16(2H,d,J=8.6 Hz), 7.18(2H,d,J=8.3 Hz), 7.32(2H,d,J=8.3 Hz), 7.34(2H,d,J=8.6 Hz), 7.48(1H,s).

IR (KBr) cm$^{-1}$: 3436,1595,1489,1383,1107,1091,833, 825.

Mass m/z: 346(M$^+$),348(M$^+$).

Example 32

Preparation of 3-[4-(methylthio)phenyl]-6-phenylthio-4-[4-(phenylthio)phenyl]pyridazine In a similar manner as in Example 2, 6-chloro-4-(4-chlorophenyl)-3-[4-(methylthio)phenyl]pyridazine (150 mg, 0.303 mmol) and thiophenol (119 mg) were reacted as starting materials at 150° C. for 20 hours and post-treatment was then conducted, whereby the title compound was obtained as a pale yellow crystalline powder (85.0 mg, 39.8%). Melting point: 53.3–56.2° C.(diethyl ether-hexane).

$^1$H-NMR (CDCl$_3$) δ: 2.48(3H,s), 6.98(2H,d,J=8.8 Hz), 7.02(1H,s), 7.12(2H,d,J=8.5 Hz), 7.14(2H,d,J=8.5 Hz), 7.28–7.58(10H,m), 7.65–7.69(2H,m).

IR (KBr) cm$^{-1}$: 1594,1489,1475,1439,1379,1336,1106, 1083,824,748,691.

Mass m/z: 494(M$^+$),496(M$^+$).

Example 33

Preparation of 4-(4-chlorophenyl)-6-(2,4-difluorophenoxy)-3-[4-(methylthio)phenyl] pyridazine In a similar manner as in Example 2, 6-chloro-4-(4-chlorophenyl)-3-[4-(methylthio)phenyl]pyridazine (230.0 mg, 0.662 mmol) and 2,4-difluorophenol were reacted as starting materials at 150° C. for 20 hours and post-treatment was then conducted, whereby the title compound was obtained as colorless plates (dichloromethane-hexane, 216.2 mg, 74.0%). Melting point: 163.2–164.0° C.

$^1$H-NMR (CDCl$_3$) δ: 2.47(3H,s), 6.89–7.03(3H,m), 7.14 (2H,d,J=8.8 Hz), 7.19(2H,d,J=8.8 Hz), 7.21(1H,s), 7.28(2H, d,J=8.8 Hz), 7.34(2H,d,J=8.8 Hz).

IR (KBr) cm$^{-1}$: 1596,1506,1492,1411,1389,1372,1247, 1212, 1142,1096.

Mass m/z: 440(M$^+$),442(M$^+$).

Example 34

Preparation of 4-(4-chlorophenyl)-6-(2,4-difluorophenoxy)-3-[4-(methylsulfonyl)phenyl] pyridazine 4-(4-Chlorophenyl)-6-(2,4-difluorophenoxy)-3-[4-(methylthio)phenyl]pyridazine (108 mg, 0.24 mmol) was dissolved in a mixed solvent of chloroform (5 ml) and acetone (30 ml), and to the resulting solution, a solution of sodium periodate (210 mg, 0.98 mmol) in water (10 ml) was added. Under cooling with ice water a solution (0.16 ml) of osmium tetraoxide (1 g, 0.03 mmol) in butanol (25 ml) was added, followed by stirring for 20 hours. Water was added to the reaction mixture, the thus-formed mixture was extracted with chloroform, and the organic layer was dried over anhydrous sodium sulfate. The solvent was distilled off and the residue was purified by chromatography on a silica gel column [hexane/ethyl acetate (2/1)]. Relevant fractions were separated and purified further by preparative thin-layer chromatography on silica gel [developing solvent: benzene/ethyl acetate (4/1)] and then crystallized from diethyl ether-hexane, whereby the title compound was obtained as a colorless crystalline powder. (71.5 mg, 61.7%). Melting point: 115.2–117.3° C.

$^1$H-NMR (CDCl$_3$) δ: 3.06(3H,s), 6.91–7.05(2H,m), 7.15 (2H,d,J=8.8 Hz), 7.28–7.34(2H,m), 7.37(2H,d,J=8.5 Hz), 7.58(2H,d,J=8.5 Hz), 7.88(2H,d,J=8.5 Hz).

IR (KBr) cm$^{-1}$: 1507,1493,1411,1390,1316,1304,1210, 1154,1093.

Mass m/z: 472(M$^+$),474(M$^+$).

Example 35

Preparation of 6-chloro-3-(3,4-dimethoxyphenyl)-4-(4-methoxyphenyl)pyridazine 6-(3,4-Dimethoxyphenyl)-5-(4-methoxyphenyl)-2H-pyridazin-3-one [WO 9925697](231 mg, 0.683 mmol) was processed in a similar manner as in Example 22, whereby the title compound was obtained as a brown amorphous solid (112 mg, 46.0%).

$^1$H-NMR (CDCl$_3$) δ; 3.71(3H,s), 3.82(3H,s), 3.89(3H,s), 6.80(1H,d,J=8.55 Hz), 6.87(2H,d,J=9.04 Hz), 6.96–7.00 (2H,m), 7.15(2H,d,J=9.04 Hz), 7.47(1H,m).

IR (KBr) cm$^{-1}$: 1607,1511,1418,1382,1252,1176,1141, 1025, 889,834,754.

Mass m/z: 456(M$^+$),458(M$^+$).

Example 36

Preparation of 3-(3,4-dimethoxyphenyl)-4-(4-methoxyphenyl)-6-(phenylthio)pyridazine To a solution of 6-chloro-3-(3,4-dimethoxyphenyl)-4-(4-methoxyphenyl)pyridazine (112 mg, 0.314 mmol) in N,N-dimethylformamide (2 ml), potassium carbonate (87 mg, 0.628 mmol) and thiophenol (42 mg, 0.377 mmol) were added, followed by stirring for 8 hours at a bath temperature of 100° C. The reaction mixture was extracted with ethyl acetate, the organic layer was washed successively with water and a saturated aqueous solution of sodium chloride (brine), and was then dried over anhydrous sodium sulfate. The solvent was distilled off. The resulting brown oil (162 mg) was separated and purified by preparative thin-layer chromatography on silica gel column [developing solvent: hexane/ethyl acetate (2/1)], whereby the title compound was obtained as a brown amorphous solid (98 mg, 72.5%).

$^1$H-NMR (CDCl$_3$) δ: 3.69(3H,s), 3.79(3H,s), 3.87(3H,s), 6.73–6.83(3H,m), 6.94(1H,dd,J=2.20,8.54 Hz), 7.00–7.05 (4H,m), 7.42–7.46(3H,m), 7.65–7.70(2H,m).

IR (KBr) cm$^{-1}$: 1605,1510,1375,1250,1024,832,749.

Mass m/z: 430(M$^+$),429(M$^+$−1).

Example 37

Preparation of 6-(2,4-difluorophenoxy)-3-(3,4-dimethoxyphenyl)-4-(4-methoxyphenyl)pyridazine In a similar manner as in Example 2, 6-chloro-3-(3,4-dimethoxyphenyl)-4-(4-methoxyphenyl)pyridazine (203 mg, 0.589 mmol) and 2,4-difluorophenol were reacted as starting materials at 150° C. for 20 hours and post-treatment was then conducted, whereby the title compound was obtained as a pale yellow amorphous solid (260 mg, quantitative).

$^1$H-NMR (CDCl$_3$) δ: 3.70(3H,s), 3.83(3H,s), 3.87(3H,s), 6.74(1H,d,J=8.55 Hz), 6.66–7.04(7H,m), 7.13–7.21(3H,m).

IR (KBr) cm$^{-1}$: 1609,1506,1391,1251,1210,1178,1140, 1026.

Mass m/z: 450(M$^+$).

Example 38

Preparation of 6-chloro-3-(3,4-ethylenedioxyphenyl)-4-(4-methoxyphenyl)pyridazine 6-(3,4-Ethylenedioxyphenyl)-5-(4-methoxyphenyl)-2H-pyridazin-3-one (202 mg, 0.601 mmol) was processed in a similar manner as in Example 22, whereby the title compound was obtained as a pale yellow amorphous solid (207 mg, 97.1%).

$^1$H-NMR (CDCl$_3$) δ: 3.83(3H,s), 4.23–4.29(4H,m), 6.74–6.80(2H,m), 6.87(2H,d,J=8.79 Hz), 7.06(1H,d,J=1.96 Hz), 7.15(2H,d,J=8.79 Hz), 7.45(1H,s).

IR (KBr) cm$^{-1}$: 1608,1510,1286,1247,1067,897,831,747.

Mass m/z: 354(M$^+$),356(M$^+$).

Example 39

Preparation of 6-(2,4-difluorophenoxy)-3-(3,4-ethylenedioxyphenyl)-4-(4-methoxyphenyl)pyridazine In a similar manner as in Example 2, 6-chloro-3-(3,4-ethylenedioxyphenyl)-4-(4-methoxyphenyl)pyridazine (136 mg, 0.383 mmol) and 2,4-difluorophenol were reacted as starting materials at 120° C. for 8 hours and post-treatment was then conducted, whereby the title compound was obtained as colorless prisms (113 mg, 65.7%). Melting point: 158.0–159.5° C. (ethyl acetate-hexane).

$^1$H-NMR (CDCl$_3$) δ: 3.84(3H,s), 4.21–4.27(4H,m), 6.07–6.80(2H,m), 6.83–7.02(5H,m), 7.18(1H,s), 7.18(2H,d,J=8.79 Hz), 7.30–7.34(1H,m).

IR (KBr) cm$^{-1}$: 1610,1505,1391,1244,1211,1062,897, 829.

Example 40

Preparation of 3,4-bis(4-methoxyphenyl)-6-(dimethylamino)pyridazine

In a similar manner as in Example 2, 3,4-bis(4-methoxyphenyl)-6-chloropyridazine (140 mg, 0.43 mmol) and a 40% (W/V) aqueous solution of dimethylamine were reacted as starting materials at 45° C. for 30 hours and post-treatment was then conducted, whereby the title compound was obtained as colorless prisms (139 mg, 96.5%). Melting point: 109.6–110.7° C. (ethyl acetate-hexane).

$^1$H-NMR (CDCl$_3$) δ: 3.23(6H,s), 3.79(3H,s), 3.81(3H,s), 6.70(1H,s), 6.78(2H,d,J=9.03 Hz), 6.84(2H,d,J=8.79 Hz), 7.13(2H,d,J=9.04 Hz), 7.31(2H,d,J=8.79 Hz).

IR (KBr) cm$^{-1}$: 1610,1591,1517,1402,1248,1173,1023, 830.

Example 41

Preparation of 6-benzylamino-3,4-bis(4-methoxyphenyl)pyridazine

In a similar manner as in Example 3,4-bis(4-methoxyphenyl)-6-chloropyridazine (300 mg, 0.918 mmol) and benzylamine were reacted as starting materials at 120° C. for 19 hours and post-treatment was then conducted, whereby the title compound was obtained as colorless prisms (365 mg, quantitative). Melting point: 125.4–126.3° C. (ethyl acetate-hexane).

$^1$H-NMR (CDCl$_3$) δ: 3.78(3H,s), 3.79(3H,s), 4.68(2H,d, J=5.62 Hz), 5.18–5.32(1H,brm), 6.51(1H,s), 6.78(2H,d,J= 8.79 Hz), 6.80(2H,d,J=8.78 Hz), 7.05(2H,d,J=8.79 Hz), 7.26–7.46(7H,m).

IR (KBr) cm$^{-1}$: 3400,3236,1611,1516,1247,1177,832.

Mass m/z: 397(M$^+$).

Example 42

Preparation of 3,4-bis-(4-methoxyphenyl)-6-(2,4-difluorophenylamino)pyridazine

In a similar manner as in Example 2, 3,4-bis-(4-methoxyphenyl)-6-chloropyridazine (264.2 mg, 0.809 mmol) and 2,4-difluoroaniline were reacted as starting materials at 100° C. for 12 hours and post-treatment was then conducted, whereby the title compound was obtained as a colorless crystalline powder (328.8 mg, 97.0%). Melting point: 177.4–178.0° C. (chloroform-diethyl ether-hexane).

$^1$H-NMR (CDCl$_3$) δ: 3.80(3H,s), 3.81(3H,s), 6.67(1H, brs), 6.81(2H,d,J=8.79 Hz), 6.84(2H,d,J=8.79 Hz), 6.85(2H, s), 6.86–6.97(2H,m), 7.11(2H,d,J=8.79 Hz), 7.33(2H,d,J= 8.79 Hz), 8.17(1H,m).

IR (KBr) cm$^{-1}$: 3419,1609,1511,1429,1250,1175.

Example 43

Preparation of 3,4-bis(4-methoxyphenyl)-6-[N-(n-propyl)-2,4-difluoroanilino]pyridazine (1) Preparation of 2',4'-difluoropropionanilide 2,4-Difluoroaniline (5.0 g, 38.7 mmol) was dissolved in chloroform (30 ml), followed by the addition of propionic anhydride (6.0 g, 46.1 mmol). The resulting mixture was stirred at room temperature for 16 hours. After methanol (10 ml) was added to the reaction mixture, the thus-obtained mixture was concentrated under reduced pressure. The residue was dissolved in chloroform. The resulting solution was washed with a saturated aqueous solution of sodium bicarbonate and was then dried over anhydrous sodium sulfate. The solvent was evaporated, and the residue was then crystallized from toluene-hexane, whereby the title compound was obtained as colorless leaflet crystals (7.17 g, quantitative). Melting point: 66.9–67;4° C.

$^1$H-NMR (CDCl$_3$) δ: 1.26(3H,t,J=7.33 Hz), 2.44(2H,q,J= 7.33 Hz), 6.82–6.91(2H,m), 7.20(1H,br), 8.28(1H,m).

IR (KBr) cm$^{-1}$: 3289,1676,1613,1546,1503,1210.

(2) Preparation of N-(n-propyl)-2,4-difluoroaniline

2',4'-Difluoropropionanilide (7.17 g, 38.7 mmol) was dissolved in tetrahydrofuran (30 ml), followed by the addition of lithium aluminum hydride (7 g, 184 mmol). The resulting mixture was stirred at 70° C. for 7 hours. Under ice-water cooling, methanol (10 ml) was added to decompose excess lithium aluminum hydride. A saturated aqueous solution of ammonium chloride (100 ml) was then added to the reaction mixture, and a precipitate was filtered off. The filtrate was extracted with chloroform, and the organic layer was dried over anhydrous sodium sulfate. The solvent was distilled off and the residue was separated and purified by chromatography on a silica gel column (silica gel 5 g, chloroform), whereby the title compound was obtained as a pale liver-brown oil (5.7 g, 86.0%).

$^1$H-NMR (CDCl$_3$) δ: 1.00(3H,t,J=7.32 Hz), 1.66(2H, sestet,J=7.32 Hz), 3.07(2H,t,J=7.32 Hz), 3.68(1H,br), 6.59 (1H,m), 6.70–6.80(2H,m).

IR (film) cm$^{-1}$: 3431,2965,2936,2877,1603,1521,1479, 1430,1264,1206,1147,1130,1092.

(3) Preparation of 3,4-bis(4-methoxyphenyl)-6-[N-(n-propyl)-2,4-difluoroanilino]pyridazine In a similar manner as in Example 2, 3,4-bis-(4-methoxyphenyl)-6-chloropyridazine (180 mg, 0.551 mmol) and N-(n-propyl)-2,4-difluoroaniline, as starting materials, were stirred 100° C. for 12 hours and then reacted at 170° C. for 10 hours, and post-treatment was then conducted, whereby the title compound was obtained as a pale yellow-brown amorphous solid (137.5 mg, 54.1%).

$^1$H-NMR (CDCl$_3$) δ: 0.86(3H,t,J=7.32 Hz), 1.79(2H, sestet,J=7.32 Hz), 3.77(3H,s), 3.79(3H,s), 4.11(2H,t,J=7.32 Hz), 6.43(1H,s), 6.76(2H,d,J=8.79 Hz), 6.78(2H,d,J=8.79 Hz), 6.96(2H,d,J=8.79 Hz), 7.14(2H,dt,J=2.45,8.06 Hz), 7.23–7.31(2H,m), 7.32(1H,d,J=8.79 Hz).

IR (KBr) cm$^{-1}$: 1610,1589,1510,1460,1426,1297,1249, 1178.

Example 44

Preparation of 3,4-bis(4-methoxyphenyl)-6-(3,4,5-trimethoxyanilino)pyridazine

In a similar manner as in Example 2, 3,4-bis(4-methoxyphenyl)-6-chloropyridazine (150.0 mg, 0.459 mmol) and 3,4,5-trimethoxy aniline were reacted as starting materials at 140° C. for 5 hours and post treatment was then conducted, whereby the title compound was obtained as a pale yellow crystalline powder (155.0 mg, 71.3%). Melting point: 125.4–126.3° C. (chloroform-hexane).

$^1$H-NMR (CDCl$_3$) δ: 3.80(3H,s), 3.81(3H,s), 3.85(3H,s), 3.86(6H,s), 6.69(2H,s), 6.81(2H,d,J=8.79 Hz), 6.82(2H,d,J= 8.79 Hz), 7.00(1H,s), 7.06(1H,brs), 7.08(2H,d,J=8.79 Hz), 7.31(2H,d,J=8.79 Hz).

IR (KBr) cm$^{-1}$: 3343,1609,1593,1574,1508,1452,1436, 1249,1128.

Example 45

Preparation of 3,4-bis(4-methoxyphenyl)-6-(morpholino)pyridazine

In a similar manner as in Example 2, 3,4-bis(4-methoxyphenyl)-6-chloropyridazine (125.5 mg, 0.384 mmol) and morpholine were reacted as starting materials at 100° C. for 15 hours and post-treatment was then conducted, whereby the title compound was obtained as a pale yellow crystalline powder (115.2 mg, 79.5%). Melting point: 188.0–190.3° C. (chloroform-diethylether).

$^1$H-NMR (CDCl$_3$) δ: 3.82(3H,s), 3.83(3H,s), 3.88(8H, brs), 6.85(2H,d,J=8.79 Hz), 6.87(2H,d,J=8.79 Hz), 7.13(2H, d,J=8.79 Hz), 7.28(1H,s), 7.34(2H,d,J=8.79 Hz).

IR (KBr) cm$^{-1}$: 1627 1606,1518,1303,1251,1189.

Example 46

Preparation of 4-(4-fluorophenyl)-6-methylthio-3-[4-(methylthio)phenyl]pyridazine A solution of 55% sodium hydride (4.3 mg, 0.097 mmol) in N,N-dimethylformamide (1 ml) was ice-cooled under an argon gas atmosphere, followed by the addition of a solution of 5-(4-fluorophenyl)-6-[4-(methylthio)phenyl]-2H-pyridazine-3-thione [WO 9925697] (32 mg, 0.097 mmol) in N,N-dimethylformamide (2 ml) and further by the addition of a solution of methyl iodide (13.9 mg, 0.097 mmol) in N,N-dimethylformamide (1 ml). The resulting mixture was then stirred for 1 hour. The reaction mixture was diluted with ethyl acetate, and the thus-obtained mixture was washed successively with an aqueous solution of sodium thiosulfate, water and brine. The organic layer was dried over anhydrous sodium sulfate. The solvent was distilled off and the residue was separated and purified by chromatography on a silica gel column [silica gel 2 g, hexane/ethyl acetate (2/1)] and relevant fractions were then crystallized from ethyl acetate-hexane, whereby crude crystals were obtained (38.1 mg). Those crude crystals were recrystallized from ethyl acetate-hexane, whereby the title compound was obtained as yellow prisms (20.9 mg, 62.9%). Melting point: 165.8–169.5° C.

$^1$H-NMR (CDCl$_3$) δ: 2.48(3H,s), 2.79(3H,s), 7.03(2H,t, J=8.55 Hz), 7.13–7.19(4H,m), 7.29(1H,s), 7.32(2H,d,J=8.30 Hz).

IR (KBr) cm 1: 1604,1508,1386,1227,1107,839.

Mass m/z: 342(M$^+$),343(M$^+$),344(M$^+$)

Example 47

Preparation of 3,4-bis(4-methoxyphenyl)-6-(methylsulfonyl)pyridazine 3,4-Bis(4-methoxyphenyl)-6-(methylthio)pyridazine (0.18 g, 0.53 mmol) was processed in a similar manner as in Example 34, whereby a pale brown oil was obtained (0.28, quantitative). The oil was crystallized from ethyl acetate-hexane, whereby the title compound was obtained as pale brown prisms. Melting point: 137–140° C.

$^1$H-NMR (CDCl$_3$) δ: 3.49(3H,s), 3.84(6H,s), 6.88(2H,d, J=8.8 Hz), 6.92(2H,d,J=8.8 Hz), 7.20(2H,d,J=8.8 Hz), 7.47 (2H,d,J=8.8 Hz), 8.09(1H,s).

IR (KBr) cm$^{-1}$: 1607,1513,1501,1323,1256,1155.

Example 48

Preparation of 3,4-bis(4-methoxyphenyl)-6-(methylsulfonyloxy)pyridazine

Methanesulfonyl chloride (10 ul. 1.44 mmol) was added to a solution of 5,6-bis(4-methoxyphenyl)-2H-pyridazine-3-one (111 mg, 0.36 mmol) in pyridine (3 ml), followed by stirring at room temperature for 5 days. Pyridine was distilled off, and to the residue, water-chloroform was added. The resulting mixture was extracted with chloroform, and the organic layer was dried over anhydrous sodium sulfate. The solvent was distilled off and the residue was separated and purified by preparative thin-layer chromatography on silica gel [developing solvent: hexane/ethyl acetate (2/1)], whereby a colorless oil was obtained (93 mg, 66.9%). The oil was crystallized from ethyl acetate-hexane, whereby the title compound was obtained as pale purplish-red prisms (59 mg). Melting point: 150.0–151.0° C.

$^1$H-NMR (CDCl$_3$) δ: 3.66(3H,s), 3.83(3H,s), 3.63(3H,s), 6.85(2H,d,J=9.03 Hz), 6.87(2H,d,J=8.79 Hz), 7.15(2H,d,J= 8.79 Hz), 7.30(1H,s), 7.37(2H,d,J=9.04 Hz).

IR (KBr) cm$^{-1}$: 1609,1513,1395,1372,1256,1180,1162, 909,816.

Example 49

Preparation of 4-(4-chlorophenyl)-6-methyl-3-[4-(methylthio)phenyl]pyridazine (1) Preparation of 4-(4-chlorophenyl)-3-buten-2-one Piperidine (1.5 ml) was added to a mixed solvent of acetone (1.1 ml) and ethanol (5 ml). After the resulting mixture was stirred for 5 minutes, 4-chlorobenzaldehyde (700 mg, 5.0 mmol) was added. The thus-obtained mixture was stirred at room temperature for 30 minutes. Acetic acid (two droplets, 0.2 ml) was then added, followed by heating under reflux for 6 hours. The solvent was distilled off and the residue (879 mg) was separated and purified by chromatography on a silica gel column [silica gel 40 g, hexane/diethylether (10/1)], whereby the title compound was obtained as a pale yellow oil (375 mg, 41.7%).

$^1$H-NMR (CDCl$_3$) δ: 2.38(3H,s), 6.71(1H,d,J=16.11 Hz), 7.34–7.50(5H,m).

(2) Preparation of 4-(4-chlorophenyl)-5-[4-(methylthio) phenyl]pentane-2,5-dione Sodium cyanide (90 mg, 1.87 mmol) was added to a solution of 4-(methylthio)benzaldehyde (300 mg, 1.97 mmol) in N,N-dimethylformamide (2 ml). While stirring the resulting mixture at 30–40° C., a solution of 4-(4-chlorophenyl)-3-buten-2-one (370 mg, 1.97 mmol) in N,N-dimethylformamide (3 ml) was dropped. The thus-obtained mixture was then stirred at the same temperature for 90 minutes. Water was added to the reaction mixture, followed by extraction with ethyl acetate. The organic layer was washed successively with water and brine, and was then dried over anhydrous sodium sulfate. The solvent was distilled off and the thus-obtained brown oil (762 mg) was separated and purified by preparative thin-layer chromatography on silica gel [developing solvent: hexane/diethyl ether (2/1)], whereby the title compound was obtained as a pale yellow oil (317 mg, 48.3%).

$^1$H-NMR (CDCl$_3$) δ: 2.18(3H,s), 2.47(3H,s), 2.72(1H,dd, J=4.15,18.07 Hz), 3.57(1H,dd J=9.77,18.07 Hz), 5.04(1H, dd,J=4.15,9.76 Hz), 7.18(2H,d,J=8.78 Hz), 7.19–7.25(4H, m), 7.85(2H,d,J=8.79 Hz).

(3) Preparation of 4-(4-chlorophenyl)-6-methyl-3-[4 (methylthio)phenyl]pyridazine Hydrazine hydrate (72 mg, 1.44 mmol) was added to a solution of 4-(4-chlorophenyl)-5-[4-(methylthio)phenyl] pentane-2,5-dione (317 mg, 0.953 mmol) in ethanol (6 ml), and the resulting mixture was stirred for 7 hours at a bath temperature of 80° C. Water was added to the reaction mixture, followed by extraction with ethyl acetate. The extract was washed successively with water and brine, and was then dried over anhydrous sodium sulfate. The solvent was distilled off and the residue (320 mg) was dissolved in chloroform. The thus-obtained solution was stirred at room temperature for 7 hours to conduct air oxidation. The solvent was distilled off and the residue (296 mg) was separated and purified by preparative thin-layer chromatography on silica gel (developing solvent: chloroform), whereby the title compound was obtained as a pale yellow oil (200.5 mg, 64.3%).

$^1$H-NMR (CDCl$_3$) δ: 2.48(3H,s), 2.80(3H,s), 7.14(2H,d, J=8.30 Hz), 7.17(2H,d,J=8.30 Hz), 7.28(1H,s), 7.32(2H,d, J=8.30 Hz), 7.34(2H,d,J=8.30 Hz).

Mass m/z: 325(M$^+$-1),326(M$^+$),327(M$^+$),328(M$^+$).

Example 50

Preparation of 4-(4-chlorophenyl)-6-methyl-3-[4-(methylsulfonyl)phenyl]pyridazine Hydrazine monohydrate (206 mg, 4.1 mmol) was added to a solution of 4-(4-chlorophenyl)-5-[4-(methylthio) phenyl]pentane-2,5-dione (661 mg, 2.0 mmol) in ethanol (12 ml), and the resulting mixture was stirred for 3 hours at a bath temperature of 80° C. The solvent was distilled off and the residue was dissolved in chloroform (30 ml). The thus-obtained solution was stirred at room temperature for 24 hours to conduct air oxidation. The solvent was distilled off, and the residue was dissolved in acetic acid (10 ml), followed by addition of hydrogen peroxide solution 31%. The resulting mixture was stirred for 3 hours at a bath temperature of 70° C. After the reaction mixture was neutralized with a dilute aqueous solution of caustic soda, the reaction mixture was extracted with ethyl acetate. The organic layer was washed successively with a 3% aqueous solution of sodium sulfite and brine, and was then dried over anhydrous sodium sulfate. The solvent was distilled off and the residue was separated and purified by preparative thin-layer chromatography on silica gel [developing solvent: chloroform/methanol (35/1)], whereby the title compound was obtained as slightly yellow prisms (330 mg, 46.3%). Melting point: 205–209° C. (ethyl acetate).

$^1$H-NMR (CDCl$_3$) δ: 2.84(3H,s), 3.07(3H,s), 7.11(2H,d, J=8.30 Hz), 7.34(2H,d,J=8.79 Hz), 7.37(1H,s), 7.63(2H,d, J=8.55 Hz), 7.91(2H,d,J=8.55 Hz).

IR (KBr) cm$^{-1}$: 1596,1391,1311,1303,1151,1091,856, 840.

Mass m/z: 357(M$^+$-1),358(M$^+$),359(M$^+$),360(M$^+$).

Example 51

Preparation of 3,4-bis-(4-methoxyphenyl)-6-cyanopyridazine

A solution of 3,4-bis-(4-methoxyphenyl)pyridazine 1-oxide [Eur. J. Med. Chem.-Chimica Therapeutica, 14, 53–60 (1979)] (5.01 g, 16.25 mmol) and potassium cyanide (3.17 g, 48.75 mmol) in water (90 ml) was ice-cooled. After benzoyl chloride (7.77 g, 55.25 mmol) was added dropwise with vigorous stirring under a nitrogen gas atmosphere, the resulting mixture was stirred at room temperature for 20 hours. Water-chloroform was added to the reaction mixture, and subsequent to alkalinization, the thus-obtained mixture was extracted with chloroform. The organic layer was washed with water, and was then dried over anhydrous sodium sulfate. The solvent was distilled off under reduced pressure and the residue (oil) was separated and purified by chromatography on a silica gel column [hexane/ethyl acetate (5/1)]. Relevant fractions were crystallized from ethyl acetate-diethyl ether-hexane, whereby the title compound was obtained as slightly yellow prisms (3.30 g, 64.0%). Melting point: 113–115° C.

$^1$H-NMR (CDCl$_3$) δ: 3.83(3H,s), 3.84(3H,s), 6.86(2H,d, J=8.2 Hz), 6.90(2H,d,J=8.2 Hz), 7.17(2H,d,J=8.2 Hz), 7.46 (2H,d,J=8.2 Hz), 7.72(1H,s).

Example 52

Preparation of 3,4-bis(4-methoxyphenyl)-6-carboxypyridazine

A 10% aqueous solution of caustic soda (9 ml) was added to a solution of 3,4-bis(4-methoxyphenyl)-6-cyanopyridazine (1.47 g, 4.63 mmol) in ethanol (12 ml), followed by stirring at 100° C. for 1 hour. After the solvent was distilled off, the residue was acidified with dilute hydrochloric acid and was then extracted with chloroform. The organic layer was washed with water and then dried over anhydrous sodium sulfate. The solvent was distilled off under reduced pressure and the residue was crystallized from ethyl acetate-diethyl ether, whereby the title compound was obtained as pale yellow needles (1.48 g, 95.0%). Melting point: 157–158° C.

$^1$H-NMR (CDCl$_3$) δ: 3.84(6H,s), 6.83(2H,d,J=8.79 Hz), 6.89(2H,d,J=8.79 Hz), 7.21(2H,d,J=8.79 Hz), 7.47(2H,d,J= 8.79 Hz), 8.26(1H,s).

Example 53

Preparation of 3,4-bis(4-methoxyphenyl)-6-(4-methyl-1-piperazinylcarbonyl)pyridazine 3,4-Bis(4-methoxyphenyl)-6-carboxypyridazine (0.10 g, 0.30 mmol) and N-methylpiperazine (0.375 g, 3.7 mmol) were suspended in a mixed solvent of N,N-dimethylformamide (2 ml) and tetrahydrofuran (3 ml), to which a 50% solution of cyclic 1-propanephosphoric anhydride (n=3) (0.33 g) in ethyl acetate was added under ice cooling. After the thus-obtained mixture was stirred at room temperature for 4 hours, water was added. The resulting mixture was extracted with ethylacetate. The organic layer was washed with water and then dried over anhydrous sodium sulfate. The solvent was distilled off under reduced pressure and the residue was washed with diethyl ether, whereby the title compound was obtained as pale brown crystals (49 mg, 39.4%). Slightly yellow powder (chloroform-hexane) Melting point: 178–181° C.

$^1$H-NMR (CDCl$_3$) δ: 2.41(3H,s), 2.57(4H,dt,J=7.8,5.0 Hz), 3.85(6H,s), 3.94(4H,t,J=5.0 Hz), 6.90(2H,d,J=8.4 Hz), 6.93(2H,d,J=8.4 Hz), 7.24(2H,d,J=8.4 Hz), 7.50(2H,d,J=8.4 Hz), 7.87(1H,s).

IR (KBr) cm$^{-1}$: 3436,1736,1645,1610,1514,1401,1300, 1254.

Example 54

Preparation of 3,4-bis(4-methoxyphenyl)-6-(morpholinocarbonyl)pyridazine

Using 3,4-bis(4-methoxyphenyl)-6-carboxypyridazine (0.25 g, 0.74 mmol), morpholine (0.65 g, 7.4 mmol), tetrahydrofuran (7 ml) and a 50% solution of cyclic 1-propanephosphoric anhydride (n=3) (1.2 g) in ethyl acetate (wt. %, product of Hoechst AG), the procedures of Example 53 were repeated likewise, whereby an oil was obtained (0.208 g, 69.0%). Crystallization was conducted from ethyl acetate-hexane, whereby the title compound was obtained as a colorless crystalline powder (0.155 g, 51.4%). Melting point: 126–128° C.

$^1$H-NMR (CDCl$_3$) δ: 3.77–3.98(8H,m), 3.83(6H,s), 6.86 (2H,d,J=8.8 Hz), 6.87(2H,d,J=9.0 Hz), 7.19(2H,d,J=8.8 Hz), 7.45(2H,d,J=9.0 Hz), 7.86(1H,s).

IR (KBr) cm$^{-1}$: 3447,1645,1608,1514,1389,1251.

Example 55

Preparation of 6-allyl-3,4-bis(4-methoxyphenyl)pyridazine

To a solution of 3,4-bis(4-methoxyphenyl)-6-chloropyridazine 1.2 g (3.7 mmol) in tetrahydrofuran (24 ml), tetrakis(triphenylphosphine)palladium (0.21 g, 0.18 mmol) was added. Under cooling with ice water under an argon gas atmosphere, a 1 M solution (11 ml) of allylmagnesium bromide in diethyl ether was added dropwise. After the resulting mixture was stirred at the same temperature for 1 hour, the temperature of the mixture was allowed to rise to room temperature, followed by further stirring for 2 hours. Water-ethyl acetate was added to the reaction mixture, and the thus-obtained mixture was extracted with ethyl acetate. The organic layer was washed with water and then dried over anhydrous sodium sulfate. The extract was concentrated under reduced pressure and the residue was left over at room temperature for 3 days. The residue was separated and purified by chromatography on a silica gel column [hexane/ethyl acetate (4/1)], whereby the title compound was obtained as a pale brown oil (0.85 g, 69.8%).

$^1$H-NMR (CDCl$_3$) δ: 3.76–3.90(2H,m), 3.83(3H,s), 3.85 (3H,s), 5.20–5.37(2H,m), 6.18(1H,m), 6.83–6.95(4H,m), 7.18(2H,d,J=8.1 Hz), 7.33(1H,s), 7.44(2H,d,J=8.1 Hz).

IR (film) cm$^{-1}$: 1609,1512,1397,1251,1179.

Example 56

Preparation of 3,4-bis(4-methoxyphenyl)-6-(3-hydroxypropyl)pyridazine

To a solution of 6-allyl-3,4-bis(4-methoxyphenyl) pyridazine (0.58 g, 1.7 mmol) in tetrahydrofuran (3 ml), a 0.5 M solution (8.7 ml) of 9-borabicyclo[3.3.1]nonane in tetrahydrofuran was added dropwise under an argon gas atmosphere while cooling the reaction system with ice-water. The resulting mixture was then stirred at room temperature for 15 hours. To the reaction mixture, water (1 ml) and then, 3 N caustic soda (3 ml) and 31% hydrogen peroxide (3 ml) were added under ice cooling, followed by stirring at room temperature for 2 hours. The reaction mixture was extracted with ethyl acetate, the organic layer was washed successively with water, a saturated aqueous solution of sodium hydrogencarbonate and water, and was then dried over anhydrous sodium sulfate. The extract was concentrated under reduced pressure and the resulting mixture was left over at room temperature for 3 days. The residue was separated and purified by chromatography on a silica gel column (ethyl acetate), whereby the title compound was obtained as a pale brown oil (0.54 g, 88.3%).

$^1$H-NMR (CDCl$_3$) δ: 2.12(2H,q,J=6.5 Hz), 3.08(1H,brs), 3.16(2H,t,J=7.3 Hz), 3.80(2H,t,J=6.5 Hz), 3.82(3H,s), 3.83 (3H,s), 6.85(2H,d,J=9.2 Hz), 6.88(2H,d,J=9.2 Hz), 7.16(2H, d,J=9.2 Hz), 7.33(1H,s), 7.41(2H d,J=9.2 Hz).

IR (film) cm$^{-1}$: 3366,1609,1513,1400,1299,1252,1179.

Example 57

Preparation of 3,4-bis-(4-methoxyphenyl)-6-(2-carboxyethyl)pyridazine 3,4-Bis(4-methoxyphenyl)-6-(3-hydroxypropyl) pyridazine (0.54 g, 1.5 mmol) was dissolved in acetone (6 ml), and subsequent to addition of Jones reagent (4.2 ml), the resulting mixture was stirred at room temperature for 8 hours. After isopropanol was added to decompose excess reagent, water was added and the thus-obtained mixture was extracted with ethyl acetate. The organic layer was washed with water, followed by back extraction with a saturated aqueous solution of sodium bicarbonate. The back extract was acidified with hydrochloric acid, followed by extraction with chloroform. The organic layer was washed with water and then dried over anhydrous sodium sulfate. The solvent was distilled off and the residue was separated and purified by chromatography on a silica gel column [chloroform/methanol (40/1)], whereby the title compound was obtained as a pale brown oil (0.21 g, 37.4%).

$^1$H-NMR (CDCl$_3$) δ: 3.05(2H,t,J=6.8 Hz), 3.35(2H,t,J= 6.8 Hz), 3.80(3H,s), 3.81(3H,s), 5.14(1H,brs), 6.83(2H,d,J= 9.0 Hz), 6.84(2H,d,J=9.0 Hz), 7.13(2H,d,J=9.0 Hz), 7.35 (2H,d,J=9.0 Hz), 7.40(1H,s).

IR (CHCl$_3$) cm$^{-1}$: 1727,1610,1514,1477.

Example 58

Preparation of 3,4-bis(4-methoxyphenyl)-6-(N-hydroxy-N-methyl-2-carbamoylethyl)pyridazine 3,4-Bis(4-methoxyphenyl)-6-(2-carboxyethyl)pyridazine (0.136 g, 0.37 mmol) and N-methylhydroxylamine hydrochloride (0.156 g, 1.87 mmol) were dissolved in N,N-dimethylformamide (4 ml). Under ice cooling, triethylamine (0.77 g, 7.608 mmol) and then, a 50% solution of cyclic 1-propanephosphoric anhydride (n=3) (0.39 g, 0.613 mmol) in ethyl acetate were added dropwise. After stirring for 1 hour, the temperature of the resulting mixture was allowed to rise to room temperature, at which the mixture was stirred for 15 hours. Water was added to the reaction mixture, and the thus-obtained mixture was extracted with ethyl acetate. The organic layer was washed successively with a saturated aqueous solution of sodium hydrogencarbonate and water, and was then dried over anhydrous sodium sulfate. The solvent was distilled off and the residue was crystallized from ethyl acetate-hexane, whereby the title compound was obtained as pale brown needles (17 mg, 13.0%). Melting point: 85–87° C.

$^1$H-NMR (CDCl$_3$) δ: 1.71(1H,brs), 3.21(2H,t,J=6.7 Hz), 3.24(3H,s), 3.48(2H,t,J=6.7 Hz), 3.84(6H,s), 6.88(4H,d,J=9.2 Hz), 7.16(2H,d,J=9.2 Hz), 7.34(2H,d,J=9.2 Hz), 7.44 (1H,s).

IR (KBr) cm$^{-1}$: 3436,1736,1645,1610,1514,1401,1300, 1254.

Example 59

Preparation of 6-chloro-3-[4-(methylthio)phenyl]-4-phenylpyridazine

6-[4-(Methylthio)phenyl]-5-phenyl-2H-pyridazin-3-one [WO 9925697] (500 mg) was processed as a starting material in a similar manner as in Example 22 (reacted at 100° C. for 2 hours), whereby the title compound was obtained quantitatively as pale brown prisms (ethyl acetate-hexane). Melting point: 157.7–158.3° C.

$^1$H-NMR (CDCl$_3$) δ: 2.47(3H,s), 7.15(2H,d,]=8.5 Hz), 7.18–7.23(2H,m), 7.33(2H,d,J=8.5 Hz), 7.35–7.42(3H,m), 7.50(1H,s).

IR (KBr) cm$^{-1}$: 1592,1401,1386,1339,1323,1136,1107, 834,788,702,585.

Mass m/z: 312(M$^+$),314(M$^+$).

Example 60

Preparation of 6-chloro-4-(4-chlorophenyl)-3-[4-(methylsulfonyl)phenyl]pyridazine 6-Chloro-4-(4-chlorophenyl)-3-[4-(methylthio)phenyl] pyridazine (230 mg) was processed in a similar manner as in Example 34, whereby the title compound was quantitatively obtained as colorless plates (ethyl acetate-hexane). Melting point: 189.6–190.5° C.

$^1$H-NMR (CDCl$_3$) δ: 3.08(3H,s), 7.12(2H,d J=8.5 Hz), 7.37(2H,d,J=8.5 Hz), 7.58(1H,s), 7.62(2H,d,J=8.8 Hz), 7.93 (2H,d,J=8.8 Hz).

IR (KBr) cm$^{-1}$: 1490,1312,1304,1152,1134,1090,852, 846,776,585.

Mass m/z: 378(M$^+$),380(M$^+$).

Example 61

Preparation of 4-(4-chlorophenyl)-3-[4-(methylsulfonyl)phenyl]pyridazine (1) Preparation of 2-(4-chlorophenyl)-1-[4-(methylthio) phenyl]-4-penten-1-one After a 2.0 M solution of lithium diisopropylamide (LDA) (36.2 ml, 72.4 mmol) was added at −20° C. to a solution of 2-(4-chlorophenyl)-1-[4-(methylthio)phenyl]-1-ethanone (20 g, 72.3 mmol) in anhydrous tetrahydrofuran (200 ml), the resulting mixture was stirred for 20 minutes while heating it to room temperature. The mixture was then cooled to −20° C., at which allyl iodide (6.67 ml, 72.9 mmol) was added, followed by stirring for 30 minutes while heating it to room temperature. Water was added to the reaction mixture, and the resulting mixture was extracted with ethyl acetate. The organic layer was dried over anhydrous sodium sulfate. The solvent was distilled off and the residue was separated and purified by chromatography on a silica gel column [silica gel 100 g, hexane/ethyl acetate (2/1)]. Relevant fractions were crystallized from diethyl ether-hexane, whereby the title compound was obtained as colorless prisms (22.85 g, 99.81).

$^1$H-NMR (CDCl$_3$) δ: 2.48(3H,s), 2.53(1H,td,J=7.32,15.38 Hz), 2.90(1H,td,J=7.32,13.92 Hz), 4.54(1H,t,J=7.32 Hz), 4.97(1H,dd,J=0.92,10.26 Hz), 5.02(1H,dd,J=0.92,17.58 Hz), 5.71(1H,m), 7.18–7.28(6H,m), 7.84(2H,dd,J=1.95,6.83 Hz).

IR (CHCl$_3$) cm$^{-1}$: 1663,1588,1553,1340,1322,1306, 1285,1264,1210,1172,1118.

(2) Preparation of 3-(4-chlorophenyl)-4-[4-(methylsulfonyl) phenyl]-4-oxo-butylaldehyde 2-(4-Chlorophenyl)-1-[4-(methylthio)phenyl]-4-penten-1-one (5.7 g, 18.0 mmol) was processed in a similar manner as in Example 34, whereby the title compound was obtained as a pale yellow amorphous solid (4.50 g, 71.3%)

$^1$H-NMR (CDCl$_3$) δ: 2.88(1H,dd,J=3.90,18.55 Hz) 3.04 (3H,s), 3.65(1H,dd,J=9.77,18.55 Hz), 5.08(1H,dd,J=3.90, 9.77 Hz), 7.19(2H,d,J=8.79 Hz), 7.29(2H,d,J=8.79 Hz), 7.97 (2H,d,J=8.79 Hz), 8.09(2H,d,J=8.79 Hz), 9.79(1H,s).

IR (film) cm$^{-1}$: 1718,1689,1493,1317,1153.

(3) Preparation of 4-(4-chlorophenyl)-3-[4-(methylsulfonyl) phenyl]pyridazine

Hydrazine hydrate (0.8 mP, 16.5 mmol) was added to a solution of 3-(4-chlorophenyl)-4-[4-(methylsulfonyl) phenyl]-4-oxo-butyraldehyde (4.5 g, 12.8 mmol) in ethanol (100 ml), followed by stirring at room temperature for 1 hour. Hydrogen peroxide solution 31% (6 ml) was added to the reaction mixture, and the resulting mixture was stirred at 60° C. for 18 hours. The mixture was concentrated under reduced pressure and the residue was separated and purified by chromatography on a silica gel column [silica gel 70 g, chloroform/methanol (50/1)], whereby the title compound was obtained as a pale yellow amorphous solid (2.60 g, 58.8%).

$^1$H-NMR (CDCl$_3$) δ: 3.08(3H,s), 7.13(2H,d,J=8.55 Hz), 7.35(2H,d,J=8.55 Hz), 7.54(1H,d,J=5.35 Hz), 7.66(2H,d,J= 8.55 Hz), 7.93(2H,d,J=8.55Hz), 9.29(1H,d,J=5.35 Hz).

IR (film) cm$^{-1}$: 1733,1684,1597,1492,1313,1153.

Example 62

Preparation of 4-(4-chlorophenyl)-3-[4-(methylsulfonyl)phenyl]pyridazine 1-oxide Hydrogen peroxide solution (31%, 5.2 ml) was added to a solution of 4-(4-chlorophenyl)-3-[4-(methylsulfonyl) phenyl]pyridazine (2.6 g, 7.55 mmol) in acetic acid (30 ml), followed by stirring at 50° C. for 6 hours. The reaction mixture was concentrated under reduced pressure, and to the residue, an aqueous solution of potassium carbonate was added. The thus-obtained mixture was extracted with chloroform, and the organic layer was dried over anhydrous sodium sulfate. The solvent was distilled off and the residue was separated and purified by chromatography on a silica gel column [silica gel 100 g, benzene/ethyl acetate (1/1)], whereby the title compound was obtained as a pale yellow amorphous solid (1.2 g, 44.1%).

¹H-NMR (CDCl₃) δ: 3.07(3H,s), 7.08(2H,d,J=8.55 Hz), 7.34(2H,d,J=8.55 Hz), 7.59(2H,d,J=8.55 Hz), 7.68(1H,d,J=6.59 Hz), 7.90(2H,d,J=8.55 Hz), 8.26(1H,d,J=6.59 Hz).

IR (film) cm⁻¹: 1683,1592,1525,1492,1314,1152.

Example 63

Preparation of 4-(4-chlorophenyl)-6-cyano-3-[4-(methylsulfonyl)phenyl]pyridazine To a solution of 4-(4-chlorophenyl)-3-[4-(methylsulfonyl)phenyl]pyridazine 1-oxide (1.1 g, 3.05 mmol) in anhydrous tetrahydrofuran (50 ml), water (30 ml), potassium cyanide (1.008 g, 15.5 mmol) and benzoyl chloride (6 ml, 51.7 mmol) were added successively, followed by stirring at room temperature for 24 hours. The reaction mixture was extracted with chloroform, and the organic layer was dried over anhydrous sodium sulfate. The solvent was distilled off, and the residue was separated and purified by chromatography on a silica gel column [silica gel 30 g, chloroform/methanol (40/1)]. Relevant fractions were crystallized from ethyl acetate-diethyl ether, whereby the title compound was obtained as pale yellow prisms (310 mg, 27.5%). Melting point: 211.4–212.5° C.

¹H-NMR (CDCl₃) δ: 3.09(3H,s), 7.14(2H,d,J=8.79 Hz), 7.41(2H,d,J=8.79 Hz), 7.69(2H,d,J=8.30 Hz), 7.88(1H,s), 7.97(2H,d,J=8.30 Hz).

IR (KBr) cm⁻¹: 2248,1597,1494,1386,1313,1151.

Example 64

Preparation of 3-(4-methoxyphenyl)-4-phenylpyridazine

10% Palladium on charcoal (1.1 g) was added to a solution of 6-chloro-3-(4-methoxyphenyl)-4-phenylpyridazine (1.53 g, 5.16 mmol) in acetic acid (25 ml) and under a hydrogen gas stream, catalytic reduction was conducted at room temperature and atmospheric pressure for 5 hours. The catalyst was filtered off, the solvent was distilled off, and a saturated aqueous solution of sodium bicarbonate was added to the residue. The thus-obtained mixture was extracted with chloroform, and the organic layer was dried over anhydrous sodium sulfate. The solvent was distilled off and the residue was crystallized from hexane, whereby the title compound was obtained as pale yellow needles (1.28 g, 94.7%). Melting point: 116.1–119.6° C.

¹H-NMR (CDCl₃) δ: 3.81(3H,s), 6.83(2H,d,J=8.79 Hz), 7.20–7.24(2H,m), 7.32–7.45(6H,m), 9.16(1H,d,J=5.12 Hz).

IR (KBr) cm⁻¹: 1607,1514,1428,1352,1300,1248,1181.

Example 65

Preparation of 3-(4-methoxyphenyl)-4-phenylpyridazine 1-oxide 3-(4-Methoxyphenyl)-4-phenylpyridazine (1.15 g, 4.39 mmol) was processed in a similar manner as in Example 62 and the residue was crystallized from chloroform-diethyl ether, whereby the title compound was obtained as pale yellow prisms (1.01 g, 82.8%). Melting point: 117.1–118.0° C.

¹H-NMR (CDCl₃) δ: 3.80(3H,s), 6.78(2H,d,J=8.79 Hz), 7.11–7.21(2H,m), 7.32–7.36(5H,m), 7.57(1H,d,J=6.59 Hz), 8.16(1H,d,J=6.59 Hz).

IR (KBr) cm⁻¹: 1607,1509,1428,1377,1346,1252,1173,1150.

Example 66

Preparation of 6-cyano-3-(4-methoxyphenyl)-4-phenylpyridazine 3-(4-Methoxyphenyl)-4-phenylpyridazine-1-oxide (1.11 g, 3.97 mmol) was processed in a similar manner as in Example 63 and the residue was crystallized from diethyl ether-hexane, whereby the title compound was obtained as pale yellow needles (593 mg, 51.7%). Melting point: 131.4–132.2° C.

¹H-NMR (CDCl₃) δ: 3.82(3H,s), 6.84(2H,d,J=8.79 Hz), 7.24(2H,dd,J=1.95,8.05 Hz), 7.36–7.43(3H,m), 7.44(2H,d, J=8.79 Hz), 7.76(1H,s).

IR (KBr) cm⁻¹: 2245,1575,1489,1381,1259,1184,1180.

Experiment 1 (Inhibitory Activity against Interleukin-1β Production)

Inhibitory activity of the compounds of the present invention, which are represented by the formula (I), against interleukin-1β production was tested by the following experiment:

HL-60 cells were cultured for 4 days until confluence on RPMI 1640 medium with 10% fetal bovine serum (FBS) added thereto. The medium was centrifuged. The supernatant was discarded, and the cells were then suspended at 1×10⁶ cells/ml on RPMI 1640 medium with 3% FBS, and lipopolysaccharide was added to give a final concentration of 10 μg/ml. The culture was inoculated at 1 ml/well to a 24-well plate. A test compound was added at 1 μl/well, followed by culturing for 3 days. Three days later, the amount of interleukin-1β in each culture was determined by ELISA. Each IC₅₀ value was determined by a comparison in yield with a control to which no test compound was added. Results on some representative compounds are shown in Table 1.

TABLE 1

| Test compound (Example No.) | IL-β (IC₅₀ μM) |
| --- | --- |
| 3 | 0.10 |
| 5 | 0.12 |
| 7 | 0.18 |
| 8 | 0.35 |
| 9 | 0.46 |
| 11 | 0.19 |
| 12 | 0.04 |
| 14 | 0.20 |
| 15 | 0.45 |
| 17 | 0.63 |
| 18 | 0.15 |
| 19 | 0.16 |
| 23 | 0.96 |
| 25 | 0.32 |
| 26 | 0.31 |
| 27 | 0.01 |
| 32 | 0.94 |
| 33 | 0.26 |
| 51 | 0.09 |
| 66 | 0.68 |
| Comp. Comp'd 1 | 32.10 |
| Comp. Comp'd 2 | 4.16 |

TABLE 1-continued

| Test compound (Example No.) | IL-β (IC$_{50}$ μM) |
| --- | --- |
| (Comp. Comp'd 1) OMe, MeO, Cl-pyridazine structure | |
| (Comp. Comp'd 2) OMe, MeO, EtOOC, Cl-pyridazine structure | |

CAPABILITY OF EXPLOITATION IN INDUSTRY

The phenylpyridazine compounds (I) and their salts, which pertain to the present invention, have excellent inhibitory activity against interleukin-1β production, and are useful as medicines such as preventives and therapeutics for immune system diseases, inflammatory diseases and ischemic diseases.

Obviously, numerous modifications and variations of the present invention are possible in light of the above teachings. It is therefore to be understood that within the scope of the appended claims, the invention may be practiced otherwise than as specifically described herein.

What is claimed is:

1. A phenylpyridazine compound represented by the following formula (I):

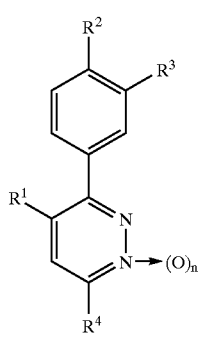

(I)

wherein
R$^1$ represents phenyl, pyridyl, substituted phenyl or substituted pyridyl, wherein the substituents are selected from the group consisting of halogen, hydroxyl, alkyl, lower alkoxy and phenylthio;
R$^2$ represents lower alkoxy, lower alkylthio, lower alkylsulfinyl or lower alkylsulfonyl;
R$^3$ represents hydrogen or lower alkoxy;
or R$^2$ and R$^3$ may be fused together to form an alkylenedioxy group;
R$^4$ represents hydrogen, halogen, cyano, carboxy, lower alkyl, lower alkyl substituted by halogen, hydroxy, cyano, nitro, amino, carboxy, aminocarbonyl, N-hydroxy,N-loweralkylaminocarbonyl or lower alkyl substituted aminocarbonyl; lower alkenyl, halogen or phenyl substituted lower alkenyl, lower alkylthio, phenyl substituted lower alkylthio, lower alkylsulfinyl, phenyl substituted lower alkylsulfinyl, lower alkylsulfonyl, phenyl substituted lower alkylsulfonyl, lower alkylsulfonyloxy, phenyl substituted lower alkylsulfonyloxy, phenyl, phenyl substituted by halogen, lower alkyl, lower alkoxy, cyano, nitro, or amino; pyridyl, pyridyl substituted by halogen, lower alkyl, lower alkoxy, cyano, nitro or amino; phenoxy, phenoxy substituted by halogen, lower alkyl, lower alkoxy, cyano, nitro or amino; phenylthio, phenylthio substituted by halogen, lower alkyl, lower alkoxy, cyano, nitro or amino; phenylsulfinyl, phenylsulfinyl substituted by halogen, lower alkyl, lower alkoxy, cyano, nitro or amino; phenylsulfonyl, phenylsulfonyl substituted by halogen, lower alkyl, lower alkoxy, cyano, nitro or amino; pyridyloxy, pyridyloxy substituted by halogen, lower alkyl, lower alkoxy, cyano, nitro or amino; morpholino, morpholino substituted by halogen, lower alkyl, lower alkoxy, cyano or nitro; morpholinocarbonyl, morpholinocarbonyl substituted by halogen, lower alkyl, lower alkoxy, cyano or nitro; piperidinocarbonyl, piperidinocarbonyl substituted by halogen, lower alkyl, lower alkoxy, cyano or nitro; 1-piperazinylcarbonyl, 1-piperazinylcarbonyl substituted by halogen, lower alkyl, lower alkoxy, cyano, nitro or amino; amino substituted by phenyl, phenyl substituted by halogen, cyano, nitro, amino, lower alkyl or lower alkoxy, or benzyl; and
n is 0 or 1,
with the proviso that when R$^1$ is 4-methoxyphenyl, R$^2$ is methoxy and R$^3$ is hydrogen, R$^4$ can not be hydrogen or halogen and with the proviso that R$^1$ can not be 4-(methylsulfonyl)phenyl or 4-(aminosulfonyl)phenyl and with the proviso that when R$^4$ is halogen, R$^1$ can not be lower alkoxyphenyl and R$^2$ can not be lower alkoxy;
or a salt thereof.

2. The phenylpyridazine compound or a salt thereof of claim 1, wherein
R$^1$ represents pyridyl, phenyl or phenyl substituted by halogen, hydroxyl, alkyl, lower alkoxy or phenylthio;
R$^2$ represents lower alkoxy, lower alkylthio or lower alkylsulfonyl;
R$^3$ represents hydrogen or lower alkoxy;
or R$^2$ and R$^3$ may be fused together to form an alkylenedioxy group;
R$^4$ represents hydrogen, halogen, cyano, carboxy, lower alkyl, lower alkyl substituted by halogen, hydroxy, cyano, nitro, amino, carboxy, aminocarbonyl, N-hydroxy,N-loweralkylaminocarbonyl or lower alkyl substituted aminocarbonyl; lower alkenyl, lower alkylthio, lower alkylsulfonyl, lower alkylsulfonyloxy, phenyl, phenyl substituted by halogen, lower alkyl, lower alkoxy, cyano, nitro or amino; pyridyl, pyridyl substituted by halogen, lower alkyl, lower alkoxy, cyano, nitro or amino; phenoxy, phenoxy substituted by halogen, lower alkyl, lower alkoxy, cyano, nitro or amino; phenylthio, phenylthio substituted by halogen, lower alkyl, lower alkoxy, cyano, nitro or amino; pyridyloxy, morpholino, morpholinocarbonyl, 1-piperazinylcarbonyl, 1-piperazinylcarbonyl substituted by halogen, lower alkyl, lower alkoxy, cyano, nitro or amino; amino substituted by phenyl, phenyl substituted by halogen, cyano, nitro, amino, lower alkyl or lower alkoxy, or benzyl; and n is 0 or 1.

3. The phenylpyridazine compound or a salt thereof according to claim 1, wherein $R^1$ represents pyridyl, or phenyl which is substituted by one or more members selected from the group consisting of hydrogen, halogen, lower alkoxy and phenylthio groups.

4. The phenylpyridazine compound or a salt thereof according to claim 1, wherein $R^4$ is hydrogen, halogen, cyano, carboxy, lower alkyl which is substituted by one or more members selected from the group consisting of hydroxyl, carboxyl, aminocarbonyl, N-hydroxy,N-loweralkylaminocarbonyl and lower alkyl substituted aminocarbonyl; lower alkenyl, lower alkylthio, lower alkylsulfonyl, lower alkylsulfonyloxy, phenyl, phenoxy which is substituted by one or more members selected from the group consisting of halogen, cyano, nitro and lower alkoxy; phenylthio which is substituted by at least one halogen atom; pyridyloxy, morpholino, morpholinocarbonyl, 1-piperazinylcarbonyl which is substituted by one or more alkyl groups; or amino which is substituted by one or more members selected from the group consisting of phenyl, phenyl substituted by halogen, cyano, nitro, amino, lower alkyl, and lower alkoxy, or benzyl.

5. The phenylpyridazine compound or a salt thereof according to claim 1, wherein the compound is a member selected from the group consisting of 3,4-bis(4-methoxyphenyl)-6-(phenoxy)pyridazine, 3,4-bis(4-methoxyphenyl)-6-(2,3-difluorophenoxy)pyridazine, 3,4-bis(4-methoxyphenyl)-6-(2,5-difluorophenoxy)pyridazine, 3,4-bis(4-methoxyphenyl)-6-(2,6-difluorophenoxy)pyridazine, 3,4-bis(4-methoxyphenyl)-6-(3,4-difluorophenoxy)pyridazine, 3,4-bis(4-methoxyphenyl)-6-(2,3,5,6-tetrafluorophenoxy)pyridazine, 3,4-bis(4methoxyphenyl)-6-(2,3,4,5,6-pentafluorophenoxy)pyridazine, 3,4-bis(4-methoxyphenyl)-6-(3,4,5-trichlorophenylthio)pyridazine, 3,4-bis(4-methoxyphenyl)-6-(4-methoxyphenoxy)pyridazine, 3,4-bis(4-methoxyphenyl)-6-(4-nitrophenoxy)pyridazine, 3,4-bis(4-methoxyphenyl)-6-(2-cyanophenoxy)pyridazine, 3,4-bis(4-methoxyphenyl)-6-(3-cyanophenoxy)pyridazine, 6-(2,4-difluorophenoxy)-3-(4-methoxyphenyl)-4-(4-pyridyl)pyridazine, 6-(2,3-difluorophenoxy)-3-(4-methoxyphenyl)-4-phenylpyridazine, 6-(2,4-difluorophenoxy)-3-(4-methoxyphenyl)-4-phenylpyridazine, 3-(4-methoxyphenyl)-6-(2,3,4,5,6-pentafluorophenoxy)-4-phenylpyridazine, 3-[4-(methylthio)phenyl]-6-phenylthio-4-[4(phenylthio)phenyl]pyridazine, 4-(4-chlorophenyl)-6-(2,4-difluorophenoxy)-3-[4-(methylthio)phenyl]pyridazine, 3,4-bis(4-methoxyphenyl)-6-cyanopyridazine, 6-cyano-3-(4-methoxyphenyl)-4-phenylpyridazine, and salts thereof.

6. The phenylpyridazine compound or a salt thereof as claimed in claim 1, wherein the salt is a member selected from the group consisting of hydrochloride, nitrate, hydrobromide, acetate, sulfate, p-toluenesulfonate, methanesulfonate, fumarate, succinate, lactate, sodium salt, potassium salt, magnesium salt, calcium salt, ammonium salt, methylammonium salt, dimethylammonium salt, and trimethylammonium.

7. A pharmaceutical composition comprising, as active ingredient, a phenylpyridazine compound as claimed in claim 1, or a pharmacologically acceptable salt thereof.

8. The pharmaceutical composition according to claim 7, wherein said composition further comprises one or more members selected from the group consisting of pharmaceutically acceptable excipients, binders, extenders, disintegrators, surfactants, lubricants, dispersants, buffers, preservatives, corrigents, perfumes, coating agents, vehicles, diluents and carriers.

9. The pharmaceutical composition according to claim 7, wherein said phenylpyridazine compound is a salt selected from the group consisting of hydrochloride, nitrate, hydrobromide, acetate, sulfate, p-toluenesulfonate, methanesulfonate, fumarate, succinate, lactate, sodium salt, potassium salt, magnesium salt, calcium salt, ammonium salt, methylammonium salt, dimethylammonium salt, and trimethylammonium.

10. The pharmaceutical composition according to claim 7, wherein $R^1$ represents pyridyl, phenyl or phenyl substituted by halogen, hydroxyl, alkyl, lower alkoxy or phenylthio;

$R^2$ represents lower alkoxy, lower alkylthio or lower alkylsulfonyl;

$R^3$ represents hydrogen or lower alkoxy;

or $R^2$ and $R^3$ may be fused together to form an alkylenedioxy group;

$R^4$ represents hydrogen, halogen, cyano, carboxy, lower alkyl, lower alkyl substituted by halogen, hydroxy, cyano, nitro, amino, carboxy, aminocarbonyl, N-hydroxy,N-loweralkylaminocarbonyl or lower alkyl substituted aminocarbonyl; lower alkenyl, lower alkylthio, lower alkylsulfonyl, lower alkylsulfonyloxy, phenyl, phenyl substituted by halogen, lower alkyl, lower alkoxy, cyano, nitro or amino; pyridyl, pyridyl substituted by halogen, lower alkyl, lower alkoxy, cyano, nitro or amino; phenoxy, phenoxy substituted by halogen, lower alkyl, lower alkoxy, cyano, nitro, or amino; phenylthio, phenylthio substituted by halogen, lower alkyl, lower alkoxy, cyano, nitro or amino; pyridyloxy, morpholino, morpholinocarbonyl, 1-piperazinylcarbonyl; 1-piperazinylcarbonyl substituted by halogen, lower alkyl, lower alkoxy, cyano, nitro or amino; or amino substituted by phenyl; phenyl substituted by halogen, cyano, nitro, amino, lower alkyl, or lower alkoxy, or benzyl; and n is 0 or 1.

11. The pharmaceutical composition according to claim 7, wherein $R^1$ is pyridyl, or phenyl which may be substituted by one or more members selected from the group consisting of halogen, lower alkoxy and phenylthio.

12. The pharmaceutical composition according to claim 7, wherein $R^4$ is hydrogen, halogen, cyano, carboxy, lower alkyl which is substituted by one or more members selected from the group consisting of hydroxyl, carboxyl, aminocarbonyl, N-hydroxy, N-loweralkylaminocarbonyl and lower alkyl substituted aminocarbonyl; lower alkenyl, lower alkylthio, lower alkylsulfonyl, lower alkylsulfonyloxy, phenyl, phenoxy which is substituted by one or more members selected from the group consisting of halogen, cyano, nitro and lower alkoxy; phenylthio which is substituted by at least one halogen atom; pyridyloxy, morpholino, morpholinocarbonyl, 1-piperazinylcarbonyl which is substituted by one or more hydrogen or alkyl groups; or amino which is substituted by one or more members selected from the group consisting of phenyl, phenyl substituted by halogen, cyano, nitro, amino, lower alkyl, and lower alkoxy, or benzyl.

13. The pharmaceutical composition according to claim 7, wherein said phenylpyridazine compound is a member selected from the group consisting of 3,4-bis(4-methoxyphenyl)-6-(phenoxy)pyridazine, 3,4-bis(4-methoxyphenyl)-6-(2,3-difluorophenoxy)pyridazine, 3,4-bis(4-methoxyphenyl)-6-(2,5-difluorophenoxy)pyridazine, 3,4-bis(4-methoxyphenyl)-6-(2,6-difluorophenoxy)pyridazine, 3,4-bis(4-methoxyphenyl)-6-(3,4-difluorophenoxy)pyridazine, 3,4-bis(4-methoxyphenyl)-6-(2,3,5,6-tetrafluorophenoxy)pyridazine, 3,4-bis(4methoxyphenyl)-6-(2,3,4,5,6-pentafluorophenoxy)pyridazine, 3,4-.bis(4-methoxyphenyl)-6-(3,4,5-trichlorophenylthio)pyridazine, 3,4-bis(4-methoxyphenyl)-6-(4-methoxyphenoxy)pyridazine, 3,4-bis(4-methoxyphenyl)-6-(4-nitrophenoxy)pyridazine, 3,4-bis(4-methoxyphenyl)-6-(2-cyanophenoxy)pyridazine, 3,4-bis(4-methoxyphenyl)-6-(3-cyanophenoxy)pyridazine, 6-(2,4-difluorophenoxy)-3-(4-methoxyphenyl)-4-(4-pyridyl)pyridazine, 6-(2,3-difluorophenoxy)-3-(4-methoxyphenyl)-4-phenylpyridazine, 6-(2,4-difluorophenoxy)-3(4-methoxyphenyl)-4-phenylpyridazine, 3-(4-methoxyphenyl)-6-(2,3,4,5,6-pentafluorophenoxy)-4-phenylpyridazine, 3-[4-(methylthio)phenyl]-6-phenylthio-4-[4(phenylthio)phenyl]pyridazine, 4-(4-chlorophenyl)-6-(2,4-difluorophenoxy)-3-[4-(methylthio)phenyl]pyridazine, 3,4-bis(4-methoxyphenyl)-6-cyanopyridazine, 6-cyano-3-(4-methoxyphenyl)-4-phenylpyridazine, and salts thereof.

14. A method for treating a disease caused by stimulation of interleukin-1β production, comprising:

administering to a subject suffering from rheumatism or arthritis an effective amount of the pharmaceutical composition according to claim 7.

15. The method according to claim 14, wherein said phenylpyridazine compound contained in said pharmaceutical composition is a salt selected from the group consisting of hydrochloride, nitrate, hydrobromide, acetate, sulfate, p-toluenesulfonate, methanesulfonate, fumarate, succinate, lactate, sodium salt, potassium salt, magnesium salt, calcium salt, ammonium salt, methylammonium salt, dimethylammonium salt, and trimethylammonium.

16. The method according to claim 14, wherein said phenylpyridazine compound contained in said pharmaceutical composition has the following substituents on formula (I):

$R^1$ represents pyridyl, phenyl or phenyl substituted by halogen, hydroxyl, alkyl, lower alkoxy or phenylthio;

$R^2$ represents lower alkoxy, lower alkylthio or lower alkylsulfonyl;

$R^3$ represents hydrogen or lower alkoxy;

or $R^2$ and $R^3$ may be fused together to form an alkylenedioxy group;

$R^4$ represents hydrogen, halogen, cyano, carboxy, lower alkyl, lower alkyl substituted by halogen, hydroxy, cyano, nitro, amino, carboxy, aminocarbonyl, N-hydroxy,N-loweralkylaminocarbonyl or lower alkyl substituted aminocarbonyl; lower alkenyl, lower alkylthio, lower alkylsulfonyl, lower alkylsulfonyloxy, phenyl, phenyl substituted by halogen, lower alkyl, lower alkoxy, cyano, nitro or amino; pyridyl, pyridyl substituted by halogen, lower alkyl, lower alkoxy, cyano, nitro or amino; phenoxy, phenoxy substituted by halogen, lower alkyl, lower alkoxy, cyano, nitro or amino; phenylthio, phenylthio which is substituted by at least one or more members selected from the group consisting of halogen atoms, lower alkyl, lower alkoxy, cyano, nitro or amino; pyridyloxy, morpholino, morpholinocarbonyl, 1-piperazinylcarbonyl, 1-piperazinylcarbonyl substituted halogen, lower alkyl groups, lower alkoxy, cyano, nitro or amino; amino which is substituted by phenyl, phenyl substituted by halogen, cyano, nitro, amino, lower alkyl, or lower alkoxy, or benzyl; and n is 0 or 1.

17. The method according to claim 14, wherein said phenylpyridazine compound contained in said pharmaceutical composition has the following substituents on formula (I):

$R^1$ is pyridyl or phenyl which is substituted by one or more members selected from the group consisting of halogen, lower alkoxy and phenylthio groups; and $R^4$ is hydrogen, halogen, cyano, carboxy, lower alkyl, which is substituted by one or more members selected from the group consisting of hydroxyl, carboxyl, aminocarbonyl, N-hydroxy,N-loweralkylaminocarbonyl and lower alkyl substituted aminocarbonyl; lower alkenyl, lower alkylthio, lower alkylsulfonyl, lower alkylsulfonyloxy, phenyl, phenoxy which is substituted by one or more members selected from the group consisting of halogen, cyano, nitro and lower alkoxy; phenylthio which is substituted by at least one halogen atom; pyridyloxy, morpholino, morpholinocarbonyl, 1-piperazinylcarbonyl, which is substituted by one or more alkyl groups; or amino, which is substituted by one or more members selected from the group consisting of phenyl, phenyl substituted by halogen, cyano, nitro, amino, lower alkyl, and lower alkoxy, or benzyl.

18. The method according to claim 14, wherein said phenylpyridazine compound contained in said pharmaceutical composition is a member selected from the group consisting of 3,4-bis(4-methoxyphenyl)-6-(phenoxy)pyridazine, 3,4-bis(4-methoxyphenyl)-6-(2,3-difluorophenoxy)pyridazine, 3,4-bis(4-methoxyphenyl)-6-(2,5-difluorophenoxy)pyridazine, 3,4-bis(4-methoxyphenyl)-6-(2,6-difluorophenoxy)pyridazine, 3,4-bis(4-methoxyphenyl)-6-(3,4-difluorophenoxy)pyridazine, 3,4-bis(4-methoxyphenyl)-6-(2,3,5,6-tetrafluorophenoxy)pyridazine, 3,4-bis(4methoxyphenyl)-6-(2,3,4,5,6-pentafluorophenoxy)pyridazine, 3,4-bis(4-methoxyphenyl)-6-(3,4,5-trichlorophenylthio)pyridazine, 3,4-bis(4-methoxyphenyl)-6-(4-methoxyphenoxy)pyridazine, 3,4-bis(4-methoxyphenyl)-6-(4-nitrophenoxy)pyridazine, 3,4-bis(4-methoxyphenyl)-6-(2-cyanophenoxy)pyridazine, 3,4-bis(4-methoxyphenyl)-6-(3-cyanophenoxy)pyridazine, 6-(2,4-difluorophenoxy)-3-(4-methoxyphenyl)-4-(4-pyridyl)pyridazine, 6-(2,3-difluorophenoxy)-3-(4-methoxyphenyl)-4-phenylpyridazine, 6-(2,4-difluorophenoxy)-3(4-methoxyphenyl)-4-phenylpyridazine, 3-(4-methoxyphenyl)-6-(2,3,4,5,6-pentafluorophenoxy)-4-phenylpyridazine, 3-[4-(methylthio)phenyl]-6-phenylthio-4-[4(phenylthio)phenyl]pyridazine, 4-(4-chlorophenyl)-6-(2,4-difluorophenoxy)-3-[4-(methylthio)phenyl]pyridazine, 3,4-bis(4-methoxyphenyl)-6-cyanopyridazine, 6-cyano-3-(4-methoxyphenyl)-4-phenylpyridazine, and salts thereof.

\* \* \* \* \*

UNITED STATES PATENT AND TRADEMARK OFFICE
CERTIFICATE OF CORRECTION

PATENT NO. : 6,664,256 B1
DATED : December 16, 2003
INVENTOR(S) : Ohkuchi et al.

It is certified that error appears in the above-identified patent and that said Letters Patent is hereby corrected as shown below:

Title page, Item [54] and Column 1, lines 1-2,
Title, should read -- PHENYLPYRIDAZINE DERIVATIVES AND MEDICINES CONTAINING THE SAME --

Title page,
Item [75], Inventors, should read:

-- [75] Inventors: Masao Ohkuchi, Tokorozawa (JP); Yoshinori Kyotani, Higashiyamato (JP); Hiromichi Shigyo, Fuchu (JP); Tomoyuki Koshi, Shiki (JP); Tadaaki Ohgiya, Tokorozawa (JP); Takayuki Matsuda, Higashimurayama (JP); Natsuyo Kumai, Fujimi (JP); Kyoko Kotaki, Sakado (JP) --

Signed and Sealed this

Eleventh Day of May, 2004

JON W. DUDAS
*Acting Director of the United States Patent and Trademark Office*